(12) United States Patent
Habicher et al.

(10) Patent No.: US 8,461,077 B2
(45) Date of Patent: Jun. 11, 2013

(54) COMBINATIONS OF ACTIVE SUBSTANCES

(75) Inventors: Christine Habicher, Speyer (DE);
Michael Merk, Limburgerhof (DE);
Egon Haden, Kleinniedesheim (DE)

(73) Assignee: BASF SE, Ludwigshafen (DE)

( * ) Notice: Subject to any disclaimer, the term of this patent is extended or adjusted under 35 U.S.C. 154(b) by 818 days.

(21) Appl. No.: 12/532,078

(22) PCT Filed: Mar. 5, 2008

(86) PCT No.: PCT/EP2008/052646
§ 371 (c)(1),
(2), (4) Date: Sep. 18, 2009

(87) PCT Pub. No.: WO2008/116730
PCT Pub. Date: Oct. 2, 2008

(65) Prior Publication Data
US 2010/0105557 A1    Apr. 29, 2010

(30) Foreign Application Priority Data
Mar. 23, 2007  (EP) .................................... 07104766

(51) Int. Cl.
*A01N 25/26*  (2006.01)
*A01N 55/02*  (2006.01)
*A01N 57/00*  (2006.01)
*A01N 43/40*  (2006.01)
*A01N 43/60*  (2006.01)

(52) U.S. Cl.
USPC ........... 504/100; 504/126; 504/127; 504/130; 504/136

(58) Field of Classification Search
None
See application file for complete search history.

(56) References Cited

U.S. PATENT DOCUMENTS

| 2008/0139581 A1 * | 6/2008 | Grammenos et al. .... 514/259.31 |
| 2008/0234295 A1 | 9/2008 | Beck et al. |
| 2009/0318291 A1 | 12/2009 | Dietz et al. |

FOREIGN PATENT DOCUMENTS

| WO | WO 2006/092428 | 9/2006 |
| WO | WO 2006092428 | * 9/2006 |
| WO | WO 2006/131230 | 12/2006 |
| WO | WO 2006131230 | * 12/2006 |
| WO | WO 2007/012598 | 2/2007 |
| WO | WO 2008/087182 | 7/2008 |

OTHER PUBLICATIONS

Orwick, P.A. et al., "A new broad spectrum herbicide—greenhouse studies", Proc. South. Weed Sci. Soc. Annu. Mtg., 36th, (1983), 291.
Tecle, B. et al., "Comparative metabolism of imidazolinone herbicides", Proc. 1997, Br. Crop Prot. Conf.—Weeds, Bd. 2, 605-610.
Warner, R.B. et al., "Tralkoxydim—A new post-emergence cereal selective graminicide", Proc. 1987 Br. Crop Prot. Conf.—Weeds, Bd. 1, 19-26.
Wixson, D. et al., "Weed control in peanut with cadre (AC 263.222) herbicide", Proc. South. Weed Sci. Soc. 1992, Bd. 45, 341.

* cited by examiner

*Primary Examiner* — Alton Pryor
(74) *Attorney, Agent, or Firm* — Brinks Hofer Gilson & Lione

(57) ABSTRACT

The present invention relates to novel active substance combinations which comprise firstly a known herbicide selected from among glyphosate derivatives, cyclohexenone oximes, imidazolinone derivatives, dinitroaniline derivatives, amide derivatives and quaternary ammonium salts, and at least one fungicidal active substance, and which are suitable for controlling undesirable phytopathogenic fungi, in particular soybean rust.

27 Claims, No Drawings

COMBINATIONS OF ACTIVE SUBSTANCES

This application is a National Stage application of International Application No. PCT/EP2008/052646 filed Mar. 5, 2008, the entire contents of which is hereby incorporated herein by reference. This application also claims the benefit under 35 U.S.C. §119 of European Patent Application No. 07104766.6, filed Mar. 23, 2007, the entire contents of which is hereby incorporated herein by reference.

The present invention relates to novel active substance combinations which comprise firstly a known herbicide selected from among glyphosate, glufosinate or glufosinate-ammonium, and secondly at least one known fungicidal active substance, and which are highly suitable for controlling undesirable phytopathogenic fungi, in particular soybean rust. The application of these mixtures to transgenic plants which are resistant to the abovementioned herbicides is especially preferred.

It has already been disclosed that glyphosate, glufosinate and glufosinate-ammonium have herbicidal properties (cf. DE-A 21 52 826, DE-A 27 17 440). It has furthermore been disclosed that azolopyrimidines of the formula II can be employed for controlling fungi (cf. EP-A 71 792; EP-A 141 317; WO 03/009687; WO 05/087771; WO 05/087772; WO 05/087773; PCT/EP/05/002426; PCT/EP2006/050922; PCT/EP2006/060399). However, the activity of these substances is not always satisfactory when low application rates are employed.

There have now been found novel active substance combinations with very good fungicidal properties, comprising
1) at least one herbicide selected from the following groups
   A) glyphosate derivatives I.A, such as
      a) glyphosate (disclosed in DE-A 21 52 826), of the formula I.Aa,

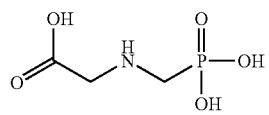

b) glufosinate (disclosed in DE-A 27 174401 of the formula I.Ab,

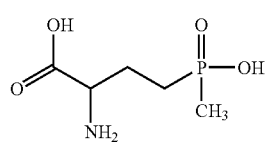

c) glufosinate-ammonium (known from Pesticide Manual, 13th edition, British Crop Protection Council, 2003, page 511-512), of the formula I.Ac,

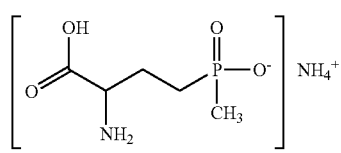

B) cyclohexenone oximes I.B, such as
      a) cycloxydim (disclosed in EP-A 71 707), of the formula I.Ba,

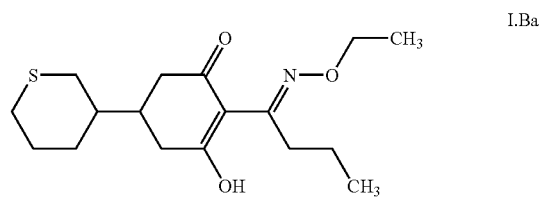

b) clethodim (disclosed in GB 2 090 246), of the formula I.Bb,

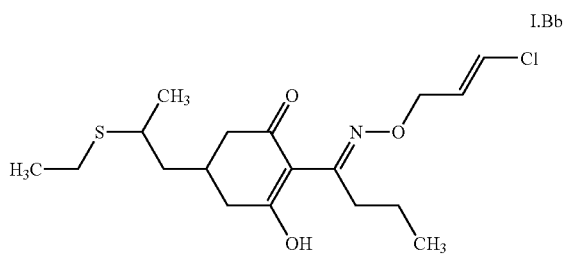

c) sethoxydim (disclosed in DE 28 22 304), of the formula I.Bc,

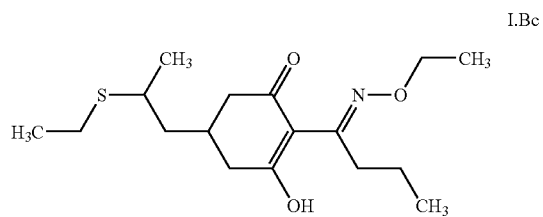 [SMILES: CCC/C(=N\OCC)C1=C(O)CC(CC(C)SCC)CC1=O]

d) profoxydim (disclosed in EP-A 456 112), of the formula I.Bd,

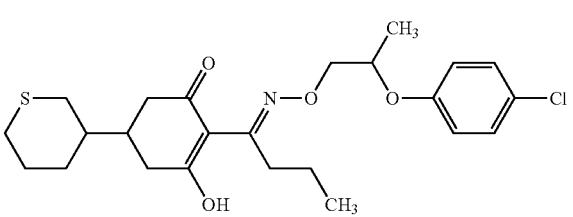

e) tralkoxydim (known from Proc. 1987 Br. Crop Prot. Conf.—Weeds, Vol. 1, p. 19), of the formula I.Be,

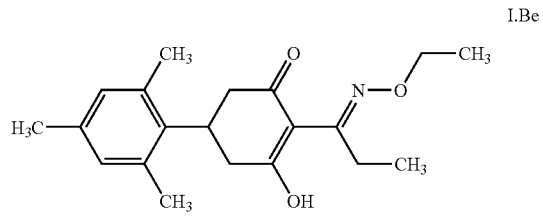 [SMILES: CCO/N=C(\CC)C1=C(O)CC(c2c(C)cc(C)cc2C)CC1=O]

C) imidazolinone derivatives I.C, such as
  a) imazapyr (known from Proc. South. Weed Sci. Soc. Annu. Mtg., 36th, 1983, p. 291), of the formula I.Ca,

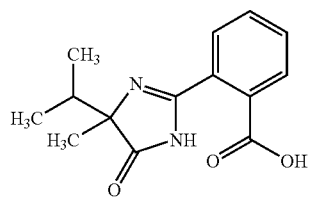

I.Ca b) imazethapyr (disclosed in U.S. Pat. No. 4,798,619), of the formula I.Cb,

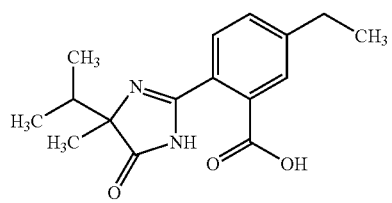

I.Cb c) imazaquin (disclosed in U.S. Pat. No. 4,798,619), of the formula I.Cc,

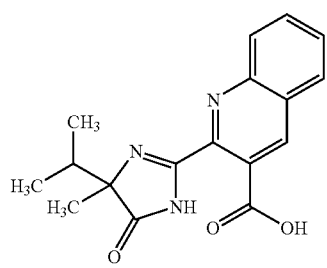

I.Cc d) imazapic (known from Proc. South. Weed Sci. Soc., 1992, Vol. 45, p. 341), of the formula I.Cd,

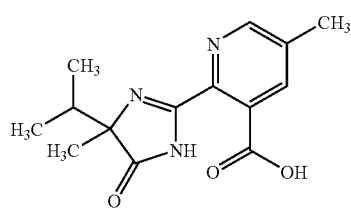

I.Cd e) imazamox (known from Proc. 1997 Br. Crop Prot. Conf.—Weeds, Vol. 2, p. 605), of the formula I.Ce,

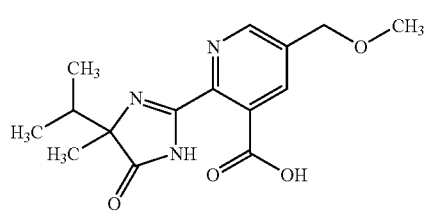

I.Ce

D) dinitroaniline derivatives I.D, such as
  a) pendimethalin (disclosed in U.S. Pat. No. 4,199,669), of the formula I.Da,

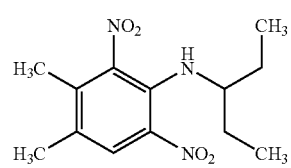

I.Da

E) amide derivatives I.E, such as
  a) dimethenamid-P (disclosed in U.S. Pat. No. 4,199,669), of the formula I.Ea,

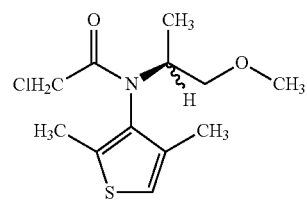

I.Ea

F) quaternary ammonium salts I.F, such as
  a) paraquat (disclosed in GB 813 531), of the formula I.Fa,

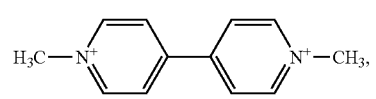

I.Fa preferably in the form of the dichloride,
  and
2) at least one azolopyrimidinylamine of the formula II

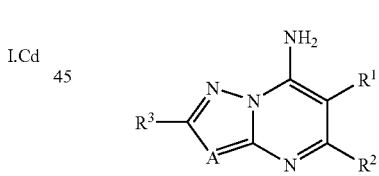

II in which the substituents have the following meanings:
    $R^1$ is $C_2$-$C_{12}$-alkyl, $C_2$-$C_{12}$-alkenyl, $C_5$-$C_{12}$-alkoxyalkyl, $C_3$-$C_6$-cycloalkyl, phenyl or phenyl-$C_1$-$C_4$-alkyl;
    $R^2$ is $C_1$-$C_{12}$-alkyl, $C_2$-$C_{12}$-alkenyl, $C_1$-$C_4$-alkoxy-$C_1$-$C_4$-alkyl;
      it being possible for the aliphatic chains in $R^1$ and/or $R^2$ to be substituted by one to four identical or different groups $R^a$:
      $R^a$ halogen, cyano, hydroxyl, mercapto, $C_1$-$C_{10}$-alkyl, $C_1$-$C_{10}$-haloalkyl, $C_3$-$C_8$-cycloalkyl, $C_2$-$C_{10}$-alkenyl, $C_2$-$C_{10}$-alkynyl, $C_1$-$C_6$-alkoxy, $C_1$-$C_6$-alkylthio, $C_1$-$C_6$-alkoxy-$C_1$-$C_6$-alkyl or $NR^AR^B$;
      $R^A$, $R^B$ hydrogen and $C_1$-$C_6$-alkyl;
      it being possible for the cyclic groups in $R^1$ and/or $R^a$ to be substituted by one to four groups $R^b$:
      $R^b$ halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl and $C_1$-$C_6$-alkoxy;

$R^3$ is hydrogen, halogen, cyano, $NR^AR^B$, hydroxyl, mercapto, $C_1$-$C_6$-alkyl, $C_1$-$C_6$-haloalkyl, $C_3$-$C_8$-cycloalkyl, $C_1$-$C_6$-alkoxy, $C_1$-$C_6$-alkylthio, $C_3$-$C_8$-cycloalkoxy, $C_3$-$C_8$-cycloalkylthio, carboxyl, formyl, $C_1$-$C_{10}$-alkylcarbonyl, $C_1$-$C_{10}$-alkoxycarbonyl, $C_2$-$C_{10}$-alkenyloxycarbonyl, $C_2$-$C_{10}$-alkynyloxycarbonyl, phenyl, phenoxy, phenylthio, benzyloxy, benzylthio, $C_1$-$C_6$-alkyl-S$(O)_m$—;

m is 0, 1 or 2;

A is CH or N;

and their agriculturally tolerated salts in synergistically active amounts.

Surprisingly, the fungicidal activity of the active substance combinations according to the invention is greater than the total of the activities of the individual active substances. This means that a synergistic effect which could not have been predicted exists, not a simple complemental of activity.

One embodiment of the invention relates to active substance combinations which comprise, besides a) glyphosate, one or more, preferably one, mixing partner of the formula II.

A further embodiment of the invention relates to active substance combinations which comprise, besides b) glufosinate, one or more, preferably one, mixing partner of the formula II.

A further embodiment of the invention relates to active substance combinations which comprise, besides c) glufosinate-ammonium, one or more, preferably one, mixing partner of the formula II.

With regard to their intended use as mixing partners, the following meanings of the substituents in the formula II are especially preferred, in each case alone or in combination:

Compounds of the formula II which are especially suitable for the mixtures according to the invention are those in which $R^1$ is straight-chain or branched $C_3$-$C_{12}$-alkyl or phenyl which can be substituted by one to three halogen or $C_1$-$C_4$-alkyl groups.

In one embodiment of the compounds of the formula II, no group $R^a$ is present.

One preferred embodiment relates to compounds of the formula II in which $R^1$ is straight-chain or branched $C_5$-$C_{10}$-alkyl, in particular ethyl, 3,5,5-trimethylhexyl, n-heptyl, n-octyl, n-nonyl and n-decyl.

A further embodiment relates to compounds of the formula II in which $R^1$ is phenyl which is unsubstituted or substituted by one to four groups halogen, cyano, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl and $C_1$-$C_6$-alkoxy.

Preferred compounds of the formula II are those in which $R^1$ is a substituted phenyl group which corresponds to a group G

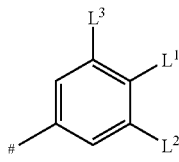

in which $L^1$ is cyano, halogen, hydroxyl, mercapto, nitro, $NR^AR^B$, $C_1$-$C_{10}$-alkyl, $C_1$-$C_6$-haloalkyl, $C_2$-$C_6$-alkenyl, $C_2$-$C_6$-alkynyl and $C_1$-$C_6$-alkoxy; and $L^2$, $L^3$ independently of one another are hydrogen or one of the groups mentioned for $L^1$, and \# marks the bond to the azolopyrimidine skeleton.

In a further embodiment of the compounds of the formula II, $L^1$ is cyano, halogen, hydroxyl, mercapto, nitro, $NR^AR^B$, $C_1$-$C_6$-alkyl, halomethyl and $C_1$-$C_2$-alkoxy, preferably cyano, halogen, $C_1$-$C_6$-alkyl, halomethyl and $C_1$-$C_2$-alkoxy.

In a further embodiment of the compounds of the formula II, $L^2$ is hydrogen or one of the abovementioned groups.

In a further embodiment of the compounds of the formula II, $L^3$ is hydrogen, cyano, halogen, hydroxyl, mercapto, nitro, $NR^AR^B$, $C_1$-$C_6$-alkyl, halomethyl or $C_1$-$C_2$-alkoxy, preferably hydrogen.

Preferred compounds of the formula II are those in which $R^2$ is straight-chain or branched $C_1$-$C_{12}$-alkyl, $C_1$-$C_4$-alkoxy-$C_1$-$C_4$-alkyl or $C_1$-$C_4$-haloalkyl.

In an especially preferred embodiment of the compounds of the formula II, $R^2$ is methyl, ethyl, n-propyl, n-octyl, trifluoromethyl or methoxymethyl, in particular methyl, ethyl, trifluoromethyl or methoxymethyl.

Other preferred compounds of the formula II are those in which $R^3$ is hydrogen.

In a further embodiment of the compounds of the formula II, $R^3$ represents amino.

Another embodiment of the compounds of the formula II relates to those in which A is N. These compounds correspond to the formula IIA, in which the variables have the meanings as shown in formula II:

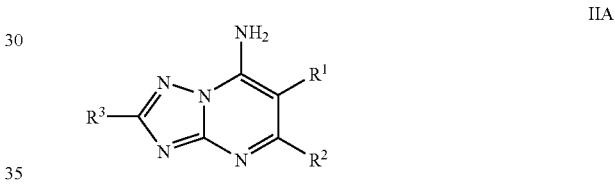

Another embodiment of the compounds of the formula II relates to those in which A is CH. These compounds correspond to the formula IIB, in which the variables have the meanings as shown in formula II:

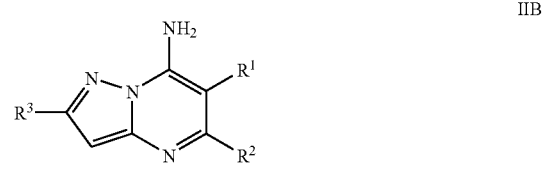

In a further embodiment of preferred compounds II, the carbon chains of $R^1$ and $R^2$ together have not more than 12 carbon atoms.

With regard to their use, the compounds II which are compiled in the tables which follow are especially preferred. Moreover, the groups mentioned in the tables for a substituent represent per se an especially preferred embodiment of the substituent in question, independently of the combination in which they are mentioned.

Table 1

Compounds of the formula IIA in which the combination of $R^1$, $R^2$ and $R^3$ for one compound corresponds in each case to one line of Table I Table 2

Compounds of the formula IIB in which the combination of $R^1$, $R^2$ and $R^3$ for one compound corresponds in each case to one line of Table I

TABLE I

| No. | R¹ | R² | R³ |
|---|---|---|---|
| I-1 | C₆H₅ | CH₃ | H |
| I-2 | 2-Cl—C₆H₄ | CH₃ | H |
| I-3 | 3-Cl—C₆H₄ | CH₃ | H |
| I-4 | 4-Cl—C₆H₄ | CH₃ | H |
| I-5 | 2-F—C₆H₄ | CH₃ | H |
| I-6 | 3-F—C₆H₄ | CH₃ | H |
| I-7 | 4-F—C₆H₄ | CH₃ | H |
| I-8 | 2,4-Cl₂—C₆H₃ | CH₃ | H |
| I-9 | 3,4-Cl₂—C₆H₃ | CH₃ | H |
| I-10 | 2,4-F₂—C₆H₃ | CH₃ | H |
| I-11 | 3,4-F₂—C₆H₃ | CH₃ | H |
| I-12 | 4-CH₃—C₆H₄ | CH₃ | H |
| I-13 | 4-CH₂CH₃—C₆H₄ | CH₃ | H |
| I-14 | 4-CH₂CH₂CH₃—C₆H₄ | CH₃ | H |
| I-15 | 4-CH(CH₃)₂—C₆H₄ | CH₃ | H |
| I-16 | 4-CH₂CH₂CH₂CH₃—C₆H₄ | CH₃ | H |
| I-17 | 4-C(CH₃)CH₂CH₃—C₆H₄ | CH₃ | H |
| I-18 | 4-C(CH₃)₃—C₆H₄ | CH₃ | H |
| I-19 | CH₂CH₂CH₂CH₃ | CH₃ | H |
| I-20 | CH₂CH₂CH₂CH₂CH₃ | CH₃ | H |
| I-21 | CH₂CH₂CH₂CH₂CH₂CH₃ | CH₃ | H |
| I-22 | CH₂CH(CH₃)CH₂CH₂CH₃ | CH₃ | H |
| I-23 | CH₂CH(CH₂CH₃)₂ | CH₃ | H |
| I-24 | CH₂CH₂CH₂CH₂CH₂CH₂CH₃ | CH₃ | H |
| I-25 | CH₂CH₂CH₂CH₂CH₂CH₂CH₂CH₃ | CH₃ | H |
| I-26 | CH₂CH₂CH₂CH₂CH₂CH₂CH₂CH₂CH₃ | CH₃ | H |
| I-27 | CH₂CH₂CH₂CH₂CH₂CH₂CH₂CH₂CH₂CH₃ | CH₃ | H |
| I-28 | CH₂CH₂CH(CH₃)CH₂CH(CH₃)₃ | CH₃ | H |
| I-29 | CH₂CH₂CH₂CH₃ | CH₃ | NH₂ |
| I-30 | CH₂CH₂CH₂CH₂CH₃ | CH₃ | NH₂ |
| I-31 | CH₂CH₂CH₂CH₂CH₂CH₃ | CH₃ | NH₂ |
| I-32 | CH₂CH(CH₃)CH₂CH₂CH₃ | CH₃ | NH₂ |
| I-33 | CH₂CH(CH₂CH₃)₂ | CH₃ | NH₂ |
| I-34 | CH₂CH₂CH₂CH₂CH₂CH₂CH₃ | CH₃ | NH₂ |
| I-35 | CH₂CH₂CH₂CH₂CH₂CH₂CH₂CH₃ | CH₃ | NH₂ |
| I-36 | CH₂CH₂CH₂CH₂CH₂CH₂CH₂CH₂CH₃ | CH₃ | NH₂ |
| I-37 | CH₂CH₂CH₂CH₂CH₂CH₂CH₂CH₂CH₂CH₃ | CH₃ | NH₂ |
| I-38 | CH₂CH₂CH(CH₃)CH₂CH(CH₃)₃ | CH₃ | NH₂ |
| I-39 | CH₂CH₂CH₂CH₃ | CH₃ | CH₃ |
| I-40 | CH₂CH₂CH₂CH₂CH₃ | CH₃ | CH₃ |
| I-41 | CH₂CH₂CH₂CH₂CH₂CH₃ | CH₃ | CH₃ |
| I-42 | CH₂CH(CH₃)CH₂CH₂CH₃ | CH₃ | CH₃ |
| I-43 | CH₂CH(CH₂CH₃)₂ | CH₃ | CH₃ |
| I-44 | CH₂CH₂CH₂CH₂CH₂CH₂CH₃ | CH₃ | CH₃ |
| I-45 | CH₂CH₂CH₂CH₂CH₂CH₂CH₂CH₃ | CH₃ | CH₃ |
| I-46 | CH₂CH₂CH₂CH₂CH₂CH₂CH₂CH₂CH₃ | CH₃ | CH₃ |
| I-47 | CH₂CH₂CH₂CH₂CH₂CH₂CH₂CH₂CH₂CH₃ | CH₃ | CH₃ |
| I-48 | CH₂CH₂CH(CH₃)CH₂CH(CH₃)₃ | CH₃ | CH₃ |
| I-49 | (CH₂)₃—O—CH₃ | CH₃ | H |
| I-50 | (CH₂)₃—O—CH₂CH₃ | CH₃ | H |
| I-51 | (CH₂)₃—O—CH₂CH₂CH₃ | CH₃ | H |
| I-52 | (CH₂)₃—O—CH₂CH₂CH₂CH₃ | CH₃ | H |
| I-53 | (CH₂)₃—O—CH₂CH₂CH₂CH₂CH₃ | CH₃ | H |
| I-54 | (CH₂)₃—O—CH₂CH₂CH₂CH₂CH₂CH₃ | CH₃ | H |
| I-55 | (CH₂)₃—O—CH₂CH₂CH₂CH₂CH₂CH₂CH₃ | CH₃ | H |
| I-56 | (CH₂)₃—O—CH₂CH₂CH₂CH₂CH₂CH₂CH₂CH₃ | CH₃ | H |
| I-57 | (CH₂)₃—O—CH₂CH₂CH₂CH₂CH₂CH₂CH₂CH₂CH₃ | CH₃ | H |
| I-58 | (CH₂)₃—O—CH(CH₃)₂ | CH₃ | H |
| I-59 | (CH₂)₃—O—C(CH₃)₃ | CH₃ | H |
| I-60 | (CH₂)₃—O—CH₂C(CH₃)₃ | CH₃ | H |
| I-61 | (CH₂)₃—O—CH(CH₃)CH₂C(CH₃)₃ | CH₃ | H |
| I-62 | (CH₂)₃—O—CH(CH₂CH₃)CH₂C(CH₃)₃ | CH₃ | H |
| I-63 | (CH₂)₃—O—CH₂CH(CH₃)CH₂CH(CH₃)₂ | CH₃ | H |
| I-64 | (CH₂)₃—O—CH₂CH(CH₂CH₃)CH₂CH₂CH₃ | CH₃ | H |
| I-65 | (CH₂)₃—O—CH₂CH₂CH(CH₃)CH₂CH(CH₃)₂ | CH₃ | H |
| I-66 | (CH₂)₃—O—CH₂CH₂CH(CH₃)CH₂C(CH₃)₃ | CH₃ | H |
| I-67 | (CH₂)₃—O—CH₂CH₂CH(CH₃)CH₂CH₂CH(CH₃)₂ | CH₃ | H |
| I-68 | (CH₂)₃—O—CH₂CH₂CH(CH₃)CH₂CH₂CH₂CH(CH₃)₂ | CH₃ | H |
| I-69 | (CH₂)₃—O—CH₃ | CH₃ | CH₃ |
| I-70 | (CH₂)₃—O—CH₂CH₃ | CH₃ | CH₃ |
| I-71 | (CH₂)₃—O—CH₂CH₂CH₃ | CH₃ | CH₃ |
| I-72 | (CH₂)₃—O—CH₂CH₂CH₂CH₃ | CH₃ | CH₃ |
| I-73 | (CH₂)₃—O—CH₂CH₂CH₂CH₂CH₃ | CH₃ | CH₃ |
| I-74 | (CH₂)₃—O—CH₂CH₂CH₂CH₂CH₂CH₃ | CH₃ | CH₃ |
| I-75 | (CH₂)₃—O—CH₂CH₂CH₂CH₂CH₂CH₂CH₃ | CH₃ | CH₃ |
| I-76 | (CH₂)₃—O—CH₂CH₂CH₂CH₂CH₂CH₂CH₂CH₃ | CH₃ | CH₃ |
| I-77 | (CH₂)₃—O—CH₂CH₂CH₂CH₂CH₂CH₂CH₂CH₂CH₃ | CH₃ | CH₃ |
| I-78 | (CH₂)₃—O—CH(CH₃)₂ | CH₃ | CH₃ |

TABLE I-continued

| No. | R¹ | R² | R³ |
|---|---|---|---|
| I-79 | (CH₂)₃—O—C(CH₃)₃ | CH₃ | CH₃ |
| I-80 | (CH₂)₃—O—CH₂C(CH₃)₃ | CH₃ | CH₃ |
| I-81 | (CH₂)₃—O—CH(CH₃)CH₂C(CH₃)₃ | CH₃ | CH₃ |
| I-82 | (CH₂)₃—O—CH(CH₂CH₃)CH₂C(CH₃)₃ | CH₃ | CH₃ |
| I-83 | (CH₂)₃—O—CH₂CH(CH₃)CH₂CH(CH₃)₂ | CH₃ | CH₃ |
| I-84 | (CH₂)₃—O—CH₂CH(CH₂CH₃)CH₂CH₂CH₃ | CH₃ | CH₃ |
| I-85 | (CH₂)₃—O—CH₂CH₂CH(CH₃)CH₂CH(CH₃)₂ | CH₃ | CH₃ |
| I-86 | (CH₂)₃—O—CH₂CH₂CH(CH₃)CH₂C(CH₃)₃ | CH₃ | CH₃ |
| I-87 | (CH₂)₃—O—CH₂CH₂CH(CH₃)CH₂CH₂CH(CH₃)₂ | CH₃ | CH₃ |
| I-88 | (CH₂)₃—O—CH₂CH₂CH(CH₃)CH₂CH₂CH₂CH(CH₃)₂ | CH₃ | CH₃ |
| I-89 | CH₂—C₆H₅ | CF₃ | H |
| I-90 | CH₂—(4-Cl—C₆H₄) | CF₃ | H |
| I-91 | CH₂CH₂CH₃ | CF₃ | H |
| I-92 | CH₂CH₂CH₂CH₃ | CF₃ | H |
| I-93 | CH₂CH₂CH₂CH₂CH₃ | CF₃ | H |
| I-94 | CH₂CH₂CH₂CH₂CH₂CH₃ | CF₃ | H |
| I-95 | CH₂CH(CH₃)CH₂CH₂CH₃ | CF₃ | H |
| I-96 | CH₂CH(CH₂CH₃)₂ | CF₃ | H |
| I-97 | CH₂CH₂CH₂CH₂CH₂CH₂CH₃ | CF₃ | H |
| I-98 | CH₂CH₂CH₂CH₂CH₂CH₂CH₂CH₃ | CF₃ | H |
| I-99 | CH₂CH₂CH₂CH₂CH₂CH₂CH₂CH₂CH₃ | CF₃ | H |
| I-100 | CH₂CH₂CH₂CH₂CH₂CH₂CH₂CH₂CH₂CH₃ | CF₃ | H |
| I-101 | CH₂CH₂CH(CH₃)CH₂CH(CH₃)₃ | CF₃ | H |
| I-102 | cyclo-C₅H₉ | CF₃ | H |
| I-103 | cyclo-C₆H₁₁ | CF₃ | H |
| I-104 | CH₂CH₂CH₂CH₃ | CH₂CH₃ | H |
| I-105 | CH₂CH₂CH₂CH₂CH₃ | CH₂CH₃ | H |
| I-106 | CH₂CH₂CH₂CH₂CH₂CH₃ | CH₂CH₃ | H |
| I-107 | CH₂CH(CH₃)CH₂CH₂CH₃ | CH₂CH₃ | H |
| I-108 | CH₂CH(CH₂CH₃)₂ | CH₂CH₃ | H |
| I-109 | CH₂CH₂CH₂CH₂CH₂CH₂CH₃ | CH₂CH₃ | H |
| I-110 | CH₂CH₂CH₂CH₂CH₂CH₂CH₂CH₃ | CH₂CH₃ | H |
| I-111 | CH₂CH₂CH₂CH₂CH₂CH₂CH₂CH₂CH₃ | CH₂CH₃ | H |
| I-112 | CH₂CH₂CH₂CH₂CH₂CH₂CH₂CH₂CH₂CH₃ | CH₂CH₃ | H |
| I-113 | CH₂CH₂CH(CH₃)CH₂CH(CH₃)₃ | CH₂CH₃ | H |
| I-114 | CH₂CH₂CH₂CH₃ | CH₂CH₃ | NH₂ |
| I-115 | CH₂CH₂CH₂CH₂CH₃ | CH₂CH₃ | NH₂ |
| I-116 | CH₂CH₂CH₂CH₂CH₂CH₃ | CH₂CH₃ | NH₂ |
| I-117 | CH₂CH(CH₃)CH₂CH₂CH₃ | CH₂CH₃ | NH₂ |
| I-118 | CH₂CH(CH₂CH₃)₂ | CH₂CH₃ | NH₂ |
| I-119 | CH₂CH₂CH₂CH₂CH₂CH₂CH₃ | CH₂CH₃ | NH₂ |
| I-120 | CH₂CH₂CH₂CH₂CH₂CH₂CH₂CH₃ | CH₂CH₃ | NH₂ |
| I-121 | CH₂CH₂CH₂CH₂CH₂CH₂CH₂CH₂CH₃ | CH₂CH₃ | NH₂ |
| I-122 | CH₂CH₂CH₂CH₂CH₂CH₂CH₂CH₂CH₂CH₃ | CH₂CH₃ | NH₂ |
| I-123 | CH₂CH₂CH(CH₃)CH₂CH(CH₃)₃ | CH₂CH₃ | NH₂ |
| I-124 | CH₂CH₂CH₃ | CH₂CH₃ | CH₃ |
| I-125 | CH₂CH₂CH₂CH₃ | CH₂CH₃ | CH₃ |
| I-126 | CH₂CH₂CH₂CH₂CH₃ | CH₂CH₃ | CH₃ |
| I-127 | CH₂CH(CH₃)CH₂CH₂CH₃ | CH₂CH₃ | CH₃ |
| I-128 | CH₂CH(CH₂CH₃)₂ | CH₂CH₃ | CH₃ |
| I-129 | CH₂CH₂CH₂CH₂CH₂CH₂CH₃ | CH₂CH₃ | CH₃ |
| I-130 | CH₂CH₂CH₂CH₂CH₂CH₂CH₂CH₃ | CH₂CH₃ | CH₃ |
| I-131 | CH₂CH₂CH₂CH₂CH₂CH₂CH₂CH₂CH₃ | CH₂CH₃ | CH₃ |
| I-132 | CH₂CH₂CH₂CH₂CH₂CH₂CH₂CH₂CH₂CH₃ | CH₂CH₃ | CH₃ |
| I-133 | CH₂CH₂CH(CH₃)CH₂CH(CH₃)₃ | CH₂CH₃ | CH₃ |
| I-134 | (CH₂)₃—O—CH₃ | CH₂CH₃ | H |
| I-135 | (CH₂)₃—O—CH₂CH₃ | CH₂CH₃ | H |
| I-136 | (CH₂)₃—O—CH₂CH₂CH₃ | CH₂CH₃ | H |
| I-137 | (CH₂)₃—O—CH₂CH₂CH₂CH₃ | CH₂CH₃ | H |
| I-138 | (CH₂)₃—O—CH₂CH₂CH₂CH₂CH₃ | CH₂CH₃ | H |
| I-139 | (CH₂)₃—O—CH₂CH₂CH₂CH₂CH₂CH₃ | CH₂CH₃ | H |
| I-140 | (CH₂)₃—O—CH₂CH₂CH₂CH₂CH₂CH₂CH₃ | CH₂CH₃ | H |
| I-141 | (CH₂)₃—O—CH₂CH₂CH₂CH₂CH₂CH₂CH₂CH₃ | CH₂CH₃ | H |
| I-142 | (CH₂)₃—O—CH₂CH₂CH₂CH₂CH₂CH₂CH₂CH₂CH₃ | CH₂CH₃ | H |
| I-143 | (CH₂)₃—O—CH(CH₃)₂ | CH₂CH₃ | H |
| I-144 | (CH₂)₃—O—C(CH₃)₃ | CH₂CH₃ | H |
| I-145 | (CH₂)₃—O—CH₂C(CH₃)₃ | CH₂CH₃ | H |
| I-146 | (CH₂)₃—O—CH(CH₃)CH₂C(CH₃)₃ | CH₂CH₃ | H |
| I-147 | (CH₂)₃—O—CH(CH₂CH₃)CH₂C(CH₃)₃ | CH₂CH₃ | H |
| I-148 | (CH₂)₃—O—CH₂CH(CH₃)CH₂CH(CH₃)₂ | CH₂CH₃ | H |
| I-149 | (CH₂)₃—O—CH₂CH(CH₂CH₃)CH₂CH₂CH₃ | CH₂CH₃ | H |
| I-150 | (CH₂)₃—O—CH₂CH₂CH(CH₃)CH₂CH(CH₃)₂ | CH₂CH₃ | H |
| I-151 | (CH₂)₃—O—CH₂CH₂CH(CH₃)CH₂C(CH₃)₃ | CH₂CH₃ | H |
| I-152 | (CH₂)₃—O—CH₂CH₂CH(CH₃)CH₂CH₂CH(CH₃)₂ | CH₂CH₃ | H |
| I-153 | (CH₂)₃—O—CH₂CH₂CH(CH₃)CH₂CH₂CH₂CH(CH₃)₂ | CH₂CH₃ | H |
| I-154 | (CH₂)₃—O—CH₃ | CH₂CH₃ | CH₃ |
| I-155 | (CH₂)₃—O—CH₂CH₃ | CH₂CH₃ | CH₃ |
| I-156 | (CH₂)₃—O—CH₂CH₂CH₃ | CH₂CH₃ | CH₃ |

TABLE I-continued

| No. | R¹ | R² | R³ |
|---|---|---|---|
| I-157 | (CH₂)₃—O—CH₂CH₂CH₂CH₃ | CH₂CH₃ | CH₃ |
| I-158 | (CH₂)₃—O—CH₂CH₂CH₂CH₃ | CH₂CH₃ | CH₃ |
| I-159 | (CH₂)₃—O—CH₂CH₂CH₂CH₂CH₃ | CH₂CH₃ | CH₃ |
| I-160 | (CH₂)₃—O—CH₂CH₂CH₂CH₂CH₂CH₃ | CH₂CH₃ | CH₃ |
| I-161 | (CH₂)₃—O—CH₂CH₂CH₂CH₂CH₂CH₂CH₃ | CH₂CH₃ | CH₃ |
| I-162 | (CH₂)₃—O—CH₂CH₂CH₂CH₂CH₂CH₂CH₂CH₃ | CH₂CH₃ | CH₃ |
| I-163 | (CH₂)₃—O—CH(CH₃)₂ | CH₂CH₃ | CH₃ |
| I-164 | (CH₂)₃—O—C(CH₃)₃ | CH₂CH₃ | CH₃ |
| I-165 | (CH₂)₃—O—CH₂C(CH₃)₃ | CH₂CH₃ | CH₃ |
| I-166 | (CH₂)₃—O—CH(CH₃)CH₂C(CH₃)₃ | CH₂CH₃ | CH₃ |
| I-167 | (CH₂)₃—O—CH(CH₂CH₃)CH₂C(CH₃)₃ | CH₂CH₃ | CH₃ |
| I-168 | (CH₂)₃—O—CH₂CH(CH₃)CH₂CH(CH₃)₂ | CH₂CH₃ | CH₃ |
| I-169 | (CH₂)₃—O—CH₂CH(CH₂CH₃)CH₂CH₂CH₃ | CH₂CH₃ | CH₃ |
| I-170 | (CH₂)₃—O—CH₂CH₂CH(CH₃)CH₂CH(CH₃)₂ | CH₂CH₃ | CH₃ |
| I-171 | (CH₂)₃—O—CH₂CH₂CH(CH₃)CH₂C(CH₃)₃ | CH₂CH₃ | CH₃ |
| I-172 | (CH₂)₃—O—CH₂CH₂CH(CH₃)CH₂CH₂CH(CH₃)₂ | CH₂CH₃ | CH₃ |
| I-173 | (CH₂)₃—O—CH₂CH₂CH(CH₃)CH₂CH₂CH₂CH(CH₃)₂ | CH₂CH₃ | CH₃ |
| I-174 | CH₂CH₂CH₂CH₃ | CH₂CH₂CH₃ | H |
| I-175 | CH₂CH₂CH₂CH₂CH₃ | CH₂CH₂CH₃ | H |
| I-176 | CH₂CH₂CH₂CH₂CH₂CH₃ | CH₂CH₂CH₃ | H |
| I-177 | CH₂CH(CH₃)CH₂CH₂CH₃ | CH₂CH₂CH₃ | H |
| I-178 | CH₂CH(CH₂CH₃)₂ | CH₂CH₂CH₃ | H |
| I-179 | CH₂CH₂CH₂CH₂CH₂CH₂CH₃ | CH₂CH₂CH₃ | H |
| I-180 | CH₂CH₂CH₂CH₂CH₂CH₂CH₂CH₃ | CH₂CH₂CH₃ | H |
| I-181 | CH₂CH₂CH₂CH₂CH₂CH₂CH₂CH₃ | CH₂CH₂CH₃ | H |
| I-182 | CH₂CH₂CH₂CH₂CH₂CH₂CH₂CH₂CH₃ | CH₂CH₂CH₃ | H |
| I-183 | CH₂CH₂CH(CH₃)CH₂CH(CH₃)₃ | CH₂CH₂CH₃ | H |
| I-184 | CH₂—O—CH₂CH₂CH₃ | CH₂CH₂CH₃ | H |
| I-185 | CH₂—O—CH₂CH₂CH₂CH₃ | CH₂CH₂CH₃ | H |
| I-186 | CH₂—O—CH₂CH₂CH₂CH₂CH₃ | CH₂CH₂CH₃ | H |
| I-187 | CH₂—O—CH₂CH₂CH₂CH₂CH₂CH₃ | CH₂CH₂CH₃ | H |
| I-188 | CH₂—O—CH₂CH₂CH₂CH₂CH₂CH₂CH₃ | CH₂CH₂CH₃ | H |
| I-189 | CH₂—O—CH₂CH₂CH₂CH₂CH₂CH₂CH₂CH₃ | CH₂CH₂CH₃ | H |
| I-190 | CH₂—O—C(CH₃)₃ | CH₂CH₂CH₃ | H |
| I-191 | CH₂—O—CH₂C(CH₃)₃ | CH₂CH₂CH₃ | H |
| I-192 | CH₂—O—CH(CH₃)CH₂C(CH₃)₃ | CH₂CH₂CH₃ | H |
| I-193 | CH₂—O—CH(CH₂CH₃)CH₂C(CH₃)₃ | CH₂CH₂CH₃ | H |
| I-194 | CH₂—O—CH₂CH(CH₃)CH₂CH(CH₃)₂ | CH₂CH₂CH₃ | H |
| I-195 | CH₂—O—CH₂CH(CH₂CH₃)CH₂CH₂CH₃ | CH₂CH₂CH₃ | H |
| I-196 | CH₂—O—CH₂CH₂CH(CH₃)CH₂CH(CH₃)₂ | CH₂CH₂CH₃ | H |
| I-197 | CH₂—O—CH₂CH₂CH(CH₃)CH₂C(CH₃)₃ | CH₂CH₂CH₃ | H |
| I-198 | CH₂—O—CH₂CH₂CH(CH₃)CH₂CH₂CH(CH₃)₂ | CH₂CH₂CH₃ | H |
| I-199 | CH₂—O—CH₂CH₂CH(CH₃)CH₂CH₂CH₂CH(CH₃)₂ | CH₂CH₂CH₃ | H |
| I-200 | (CH₂)₂—O—CH₂CH₂CH₃ | CH₂CH₂CH₃ | H |
| I-201 | (CH₂)₂—O—CH₂CH₂CH₂CH₃ | CH₂CH₂CH₃ | H |
| I-202 | (CH₂)₂—O—CH₂CH₂CH₂CH₂CH₃ | CH₂CH₂CH₃ | H |
| I-203 | (CH₂)₂—O—CH₂CH₂CH₂CH₂CH₂CH₃ | CH₂CH₂CH₃ | H |
| I-204 | (CH₂)₂—O—CH₂CH₂CH₂CH₂CH₂CH₂CH₃ | CH₂CH₂CH₃ | H |
| I-205 | (CH₂)₂—O—CH₂CH₂CH₂CH₂CH₂CH₂CH₂CH₃ | CH₂CH₂CH₃ | H |
| I-206 | (CH₂)₂—O—CH₂CH₂CH₂CH₂CH₂CH₂CH₂CH₂CH₃ | CH₂CH₂CH₃ | H |
| I-207 | (CH₂)₂—O—CH(CH₃)₂ | CH₂CH₂CH₃ | H |
| I-208 | (CH₂)₂—O—C(CH₃)₃ | CH₂CH₂CH₃ | H |
| I-209 | (CH₂)₂—O—CH₂C(CH₃)₃ | CH₂CH₂CH₃ | H |
| I-210 | (CH₂)₂—O—CH(CH₃)CH₂C(CH₃)₃ | CH₂CH₂CH₃ | H |
| I-211 | (CH₂)₂—O—CH(CH₂CH₃)CH₂C(CH₃)₃ | CH₂CH₂CH₃ | H |
| I-212 | (CH₂)₂—O—CH₂CH(CH₃)CH₂CH(CH₃)₂ | CH₂CH₂CH₃ | H |
| I-213 | (CH₂)₂—O—CH₂CH(CH₂CH₃)CH₂CH₂CH₃ | CH₂CH₂CH₃ | H |
| I-214 | (CH₂)₂—O—CH₂CH₂CH(CH₃)CH₂CH(CH₃)₂ | CH₂CH₂CH₃ | H |
| I-215 | (CH₂)₂—O—CH₂CH₂CH(CH₃)CH₂C(CH₃)₃ | CH₂CH₂CH₃ | H |
| I-216 | (CH₂)₂—O—CH₂CH₂CH(CH₃)CH₂CH₂CH(CH₃)₂ | CH₂CH₂CH₃ | H |
| I-217 | (CH₂)₂—O—CH₂CH₂CH(CH₃)CH₂CH₂CH₂CH(CH₃)₂ | CH₂CH₂CH₃ | H |
| I-218 | (CH₂)₃—O—CH₃ | CH₂CH₂CH₃ | H |
| I-219 | (CH₂)₃—O—CH₂CH₃ | CH₂CH₂CH₃ | H |
| I-220 | (CH₂)₃—O—CH₂CH₂CH₃ | CH₂CH₂CH₃ | H |
| I-221 | (CH₂)₃—O—CH₂CH₂CH₂CH₃ | CH₂CH₂CH₃ | H |
| I-222 | (CH₂)₃—O—CH₂CH₂CH₂CH₂CH₃ | CH₂CH₂CH₃ | H |
| I-223 | (CH₂)₃—O—CH₂CH₂CH₂CH₂CH₂CH₃ | CH₂CH₂CH₃ | H |
| I-224 | (CH₂)₃—O—CH₂CH₂CH₂CH₂CH₂CH₂CH₃ | CH₂CH₂CH₃ | H |
| I-225 | (CH₂)₃—O—CH₂CH₂CH₂CH₂CH₂CH₂CH₂CH₃ | CH₂CH₂CH₃ | H |
| I-226 | (CH₂)₃—O—CH₂CH₂CH₂CH₂CH₂CH₂CH₂CH₂CH₃ | CH₂CH₂CH₃ | H |
| I-227 | (CH₂)₃—O—CH(CH₃)₂ | CH₂CH₂CH₃ | H |
| I-228 | (CH₂)₃—O—C(CH₃)₃ | CH₂CH₂CH₃ | H |
| I-229 | (CH₂)₃—O—CH₂C(CH₃)₃ | CH₂CH₂CH₃ | H |
| I-230 | (CH₂)₃—O—CH(CH₃)CH₂C(CH₃)₃ | CH₂CH₂CH₃ | H |
| I-231 | (CH₂)₃—O—CH(CH₂CH₃)CH₂C(CH₃)₃ | CH₂CH₂CH₃ | H |
| I-232 | (CH₂)₃—O—CH₂CH(CH₃)CH₂CH(CH₃)₂ | CH₂CH₂CH₃ | H |
| I-233 | (CH₂)₃—O—CH₂CH(CH₂CH₃)CH₂CH₂CH₃ | CH₂CH₂CH₃ | H |
| I-234 | (CH₂)₃—O—CH₂CH₂CH(CH₃)CH₂CH(CH₃)₂ | CH₂CH₂CH₃ | H |

TABLE I-continued

| No. | R$^1$ | R$^2$ | R$^3$ |
|---|---|---|---|
| I-235 | (CH$_2$)$_3$—O—CH$_2$CH$_2$CH(CH$_3$)CH$_2$C(CH$_3$)$_3$ | CH$_2$CH$_2$CH$_3$ | H |
| I-236 | (CH$_2$)$_3$—O—CH$_2$CH$_2$CH(CH$_3$)CH$_2$CH$_2$CH(CH$_3$)$_2$ | CH$_2$CH$_2$CH$_3$ | H |
| I-237 | (CH$_2$)$_3$—O—CH$_2$CH$_2$CH(CH$_3$)CH$_2$CH$_2$CH$_2$CH(CH$_3$)$_2$ | CH$_2$CH$_2$CH$_3$ | H |
| I-238 | CH$_2$CH$_2$CH$_3$ | CH$_2$OCH$_3$ | H |
| I-239 | CH$_2$CH$_2$CH$_2$CH$_3$ | CH$_2$OCH$_3$ | H |
| I-240 | CH$_2$CH$_2$CH$_2$CH$_2$CH$_3$ | CH$_2$OCH$_3$ | H |
| I-241 | CH$_2$CH$_2$CH$_2$CH$_2$CH$_2$CH$_3$ | CH$_2$OCH$_3$ | H |
| I-242 | CH$_2$CH(CH$_3$)CH$_2$CH$_2$CH$_3$ | CH$_2$OCH$_3$ | H |
| I-243 | CH$_2$CH(CH$_2$CH$_3$)$_2$ | CH$_2$OCH$_3$ | H |
| I-244 | CH$_2$CH$_2$CH$_2$CH$_2$CH$_2$CH$_2$CH$_3$ | CH$_2$OCH$_3$ | H |
| I-245 | CH$_2$CH$_2$CH$_2$CH$_2$CH$_2$CH$_2$CH$_2$CH$_3$ | CH$_2$OCH$_3$ | H |
| I-246 | CH$_2$CH$_2$CH$_2$CH$_2$CH$_2$CH$_2$CH$_2$CH$_2$CH$_3$ | CH$_2$OCH$_3$ | H |
| I-247 | CH$_2$CH$_2$CH$_2$CH$_2$CH$_2$CH$_2$CH$_2$CH$_2$CH$_2$CH$_3$ | CH$_2$OCH$_3$ | H |
| I-248 | CH$_2$CH$_2$CH(CH$_3$)CH$_2$CH(CH$_3$)$_3$ | CH$_2$OCH$_3$ | H |
| I-249 | (CH$_2$)$_3$—O—CH$_3$ | CH$_2$OCH$_3$ | H |
| I-250 | (CH$_2$)$_3$—O—CH$_2$CH$_3$ | CH$_2$OCH$_3$ | H |
| I-251 | (CH$_2$)$_3$—O—CH$_2$CH$_2$CH$_3$ | CH$_2$OCH$_3$ | H |
| I-252 | (CH$_2$)$_3$—O—CH$_2$CH$_2$CH$_2$CH$_3$ | CH$_2$OCH$_3$ | H |
| I-253 | (CH$_2$)$_3$—O—CH$_2$CH$_2$CH$_2$CH$_2$CH$_3$ | CH$_2$OCH$_3$ | H |
| I-254 | (CH$_2$)$_3$—O—CH$_2$CH$_2$CH$_2$CH$_2$CH$_2$CH$_3$ | CH$_2$OCH$_3$ | H |
| I-255 | (CH$_2$)$_3$—O—CH$_2$CH$_2$CH$_2$CH$_2$CH$_2$CH$_2$CH$_3$ | CH$_2$OCH$_3$ | H |
| I-256 | (CH$_2$)$_3$—O—CH$_2$CH$_2$CH$_2$CH$_2$CH$_2$CH$_2$CH$_2$CH$_3$ | CH$_2$OCH$_3$ | H |
| I-257 | (CH$_2$)$_3$—O—CH$_2$CH$_2$CH$_2$CH$_2$CH$_2$CH$_2$CH$_2$CH$_2$CH$_3$ | CH$_2$OCH$_3$ | H |
| I-258 | (CH$_2$)$_3$—O—CH(CH$_3$)$_2$ | CH$_2$OCH$_3$ | H |
| I-259 | (CH$_2$)$_3$—O—C(CH$_3$)$_3$ | CH$_2$OCH$_3$ | H |
| I-260 | (CH$_2$)$_3$—O—CH$_2$C(CH$_3$)$_3$ | CH$_2$OCH$_3$ | H |
| I-261 | (CH$_2$)$_3$—O—CH(CH$_3$)CH$_2$C(CH$_3$)$_3$ | CH$_2$OCH$_3$ | H |
| I-262 | (CH$_2$)$_3$—O—CH(CH$_2$CH$_3$)CH$_2$C(CH$_3$)$_3$ | CH$_2$OCH$_3$ | H |
| I-263 | (CH$_2$)$_3$—O—CH$_2$CH(CH$_3$)CH$_2$CH(CH$_3$)$_2$ | CH$_2$OCH$_3$ | H |
| I-264 | (CH$_2$)$_3$—O—CH$_2$CH(CH$_2$CH$_3$)CH$_2$CH$_2$CH$_3$ | CH$_2$OCH$_3$ | H |
| I-265 | (CH$_2$)$_3$—O—CH$_2$CH$_2$CH(CH$_3$)CH$_2$CH(CH$_3$)$_2$ | CH$_2$OCH$_3$ | H |
| I-266 | (CH$_2$)$_3$—O—CH$_2$CH$_2$CH(CH$_3$)CH$_2$C(CH$_3$)$_3$ | CH$_2$OCH$_3$ | H |
| I-267 | (CH$_2$)$_3$—O—CH$_2$CH$_2$CH(CH$_3$)CH$_2$CH$_2$CH(CH$_3$)$_2$ | CH$_2$OCH$_3$ | H |
| I-268 | (CH$_2$)$_3$—O—CH$_2$CH$_2$CH(CH$_3$)CH$_2$CH$_2$CH$_2$CH(CH$_3$)$_2$ | CH$_2$OCH$_3$ | H |
| I-269 | CH$_3$ | (CH$_2$)$_3$CH$_3$ | H |
| I-270 | CH$_2$CH$_3$ | (CH$_2$)$_3$CH$_3$ | H |
| I-271 | CH$_2$CH$_2$CH$_3$ | (CH$_2$)$_3$CH$_3$ | H |
| I-272 | CH$_2$CH$_2$CH$_2$CH$_3$ | (CH$_2$)$_3$CH$_3$ | H |
| I-273 | CH$_2$CH$_2$CH$_2$CH$_2$CH$_3$ | (CH$_2$)$_3$CH$_3$ | H |
| I-274 | CH$_3$ | (CH$_2$)$_4$CH$_3$ | H |
| i-275 | CH$_2$CH$_3$ | (CH$_2$)$_4$CH$_3$ | H |
| I-276 | CH$_2$CH$_2$CH$_3$ | (CH$_2$)$_4$CH$_3$ | H |
| I-277 | CH$_2$CH$_2$CH$_2$CH$_3$ | (CH$_2$)$_4$CH$_3$ | H |
| I-278 | CH$_2$CH$_2$CH$_2$CH$_2$CH$_3$ | (CH$_2$)$_4$CH$_3$ | H |
| I-279 | CH$_3$ | (CH$_2$)$_5$CH$_3$ | H |
| I-280 | CH$_2$CH$_3$ | (CH$_2$)$_5$CH$_3$ | H |
| I-281 | CH$_2$CH$_2$CH$_3$ | (CH$_2$)$_5$CH$_3$ | H |
| I-282 | CH$_2$CH$_2$CH$_2$CH$_3$ | (CH$_2$)$_5$CH$_3$ | H |
| I-283 | CH$_2$CH$_2$CH$_2$CH$_2$CH$_3$ | (CH$_2$)$_5$CH$_3$ | H |
| I-284 | CH$_3$ | (CH$_2$)$_6$CH$_3$ | H |
| I-285 | CH$_2$CH$_3$ | (CH$_2$)$_6$CH$_3$ | H |
| I-286 | CH$_2$CH$_2$CH$_3$ | (CH$_2$)$_6$CH$_3$ | H |
| I-287 | CH$_2$CH$_2$CH$_2$CH$_3$ | (CH$_2$)$_6$CH$_3$ | H |
| I-288 | CH$_2$CH$_2$CH$_2$CH$_2$CH$_3$ | (CH$_2$)$_6$CH$_3$ | H |
| I-289 | CH$_3$ | (CH$_2$)$_7$CH$_3$ | H |
| I-290 | CH$_2$CH$_3$ | (CH$_2$)$_7$CH$_3$ | H |
| I-291 | CH$_2$CH$_2$CH$_3$ | (CH$_2$)$_7$CH$_3$ | H |
| I-292 | CH$_2$CH$_2$CH$_2$CH$_3$ | (CH$_2$)$_7$CH$_3$ | H |
| I-293 | CH$_2$CH$_2$CH$_2$CH$_2$CH$_3$ | (CH$_2$)$_7$CH$_3$ | H |
| I-294 | CH$_3$ | (CH$_2$)$_8$CH$_3$ | H |
| I-295 | CH$_2$CH$_3$ | (CH$_2$)$_8$CH$_3$ | H |
| I-296 | CH$_2$CH$_2$CH$_3$ | (CH$_2$)$_8$CH$_3$ | H |
| I-297 | CH$_2$CH$_2$CH$_2$CH$_3$ | (CH$_2$)$_8$CH$_3$ | H |
| I-298 | CH$_2$CH$_2$CH$_2$CH$_2$CH$_3$ | (CH$_2$)$_8$CH$_3$ | H |

Preferred embodiments of the mixtures according to the invention comprise, as active component 2, a compound selected from among:

6-(3,4-dichlorophenyl)-5-methyl-[1,2,4]triazolo[1,5-a]pyrimidin-7-ylamine [II-1], 6-(4-tert-butylphenyl)-5-methyl-[1,2,4]triazolo[1,5-a]pyrimidin-7-ylamine [II-2], 5-methyl-6-(3,5,5-trimethylhexyl)-[1,2,4]triazolo[1,5-a]pyrimidin-7-ylamine [II-3], 5-methyl-6-octyl-[1,2,4]triazolo[1,5-a]pyrimidin-7-ylamine [II-4], 5-ethyl-6-octyl-[1,2,4]triazolo[1,5-a]pyrimidin-2,7-diamine [II-5], 6-ethyl-5-octyl-[1,2,4]triazolo[1,5-a]pyrimidin-7-ylamine [II-6], 5-ethyl-6-octyl-[1,2,4]triazolo[1,5-a]pyrimidin-7-ylamine [II-7], 5-ethyl-6-(3,5,5-trimethylhexyl)-[1,2,4]triazolo[1,5-a]pyrimidin-7-ylamine [II-8], 6-octyl-5-propyl-[1,2,4]triazolo[1,5-a]pyrimidin-7-ylamine [II-9], 5-methoxymethyl-6-octyl-[1,2,4]triazolo[1,5-a]pyrimidin-7-ylamine [II-10], 6-octyl-5-trifluoromethyl-[1,2,4]triazolo[1,5-a]pyrimidin-7-ylamine [II-11] and 5-trifluoromethyl-6-(3,5,5-trimethylhexyl)-[1,2,4]triazolo[1,5-a]pyrimidin-7-ylamine [II-12].

Preferred embodiments relate to the compositions detailed in table A, where in each case one line of table A corresponds to a fungicidal composition comprising the respective herbicide (component 1) and the respective active substance of the formula II (component 2).

TABLE A

| Line | Component 1 | Component 2 |
| --- | --- | --- |
| A-1 | I.Aa | II-1 |
| A-2 | I.Ab | II-1 |
| A-3 | I.Ac | II-1 |
| A-4 | I.Ba | II-1 |
| A-5 | I.Bb | II-1 |
| A-6 | I.Bc | II-1 |
| A-7 | I.Bd | II-1 |
| A-8 | I.Be | II-1 |
| A-9 | I.Ca | II-1 |
| A-10 | I.Cb | II-1 |
| A-11 | I.Cc | II-1 |
| A-12 | I.Ce | II-1 |
| A-13 | I.Cf | II-1 |
| A-14 | I.Da | II-1 |
| A-15 | I.Ea | II-1 |
| A-16 | I.Fa | II-1 |
| A-17 | I.Aa | II-2 |
| A-18 | I.Ab | II-2 |
| A-19 | I.Ac | II-2 |
| A-20 | I.Ba | II-2 |
| A-21 | I.Bb | II-2 |
| A-22 | I.Bc | II-2 |
| A-23 | I.Bd | II-2 |
| A-24 | I.Be | II-2 |
| A-25 | I.Ca | II-2 |
| A-26 | I.Cb | II-2 |
| A-27 | I.Cc | II-2 |
| A-28 | I.Ce | II-2 |
| A-29 | I.Cf | II-2 |
| A-30 | I.Da | II-2 |
| A-31 | I.Ea | II-2 |
| A-32 | I.Fa | II-2 |
| A-33 | I.Aa | II-3 |
| A-34 | I.Ab | II-3 |
| A-35 | I.Ac | II-3 |
| A-36 | I.Ba | II-3 |
| A-37 | I.Bb | II-3 |
| A-38 | I.Bc | II-3 |
| A-39 | I.Bd | II-3 |
| A-40 | I.Be | II-3 |
| A-41 | I.Ca | II-3 |
| A-42 | I.Cb | II-3 |
| A-43 | I.Cc | II-3 |
| A-44 | I.Ce | II-3 |
| A-45 | I.Cf | II-3 |
| A-46 | I.Da | II-3 |
| A-47 | I.Ea | II-3 |
| A-48 | I.Fa | II-3 |
| A-49 | I.Aa | II-4 |
| A-50 | I.Ab | II-4 |
| A-51 | I.Ac | II-4 |
| A-52 | I.Ba | II-4 |
| A-53 | I.Bb | II-4 |
| A-54 | I.Bc | II-4 |
| A-55 | I.Bd | II-4 |
| A-56 | I.Be | II-4 |
| A-57 | I.Ca | II-4 |
| A-58 | I.Cb | II-4 |
| A-59 | I.Cc | II-4 |
| A-60 | I.Ce | II-4 |
| A-61 | I.Cf | II-4 |
| A-62 | I.Da | II-4 |
| A-63 | I.Ea | II-4 |
| A-64 | I.Fa | II-4 |
| A-65 | I.Aa | II-5 |
| A-66 | I.Ab | II-5 |
| A-67 | I.Ac | II-5 |
| A-68 | I.Ba | II-5 |
| A-69 | I.Bb | II-5 |
| A-70 | I.Bc | II-5 |
| A-71 | I.Bd | II-5 |
| A-72 | I.Be | II-5 |
| A-73 | I.Ca | II-5 |
| A-74 | I.Cb | II-5 |
| A-75 | I.Cc | II-5 |
| A-76 | I.Ce | II-5 |
| A-77 | I.Cf | II-5 |
| A-78 | I.Da | II-5 |
| A-79 | I.Ea | II-5 |
| A-80 | I.Fa | II-5 |
| A-81 | I.Aa | II-6 |
| A-82 | I.Ab | II-6 |
| A-83 | I.Ac | II-6 |
| A-84 | I.Ba | II-6 |
| A-85 | I.Bb | II-6 |
| A-86 | I.Be | II-6 |
| A-87 | I.Bd | II-6 |
| A-88 | I.Be | II-6 |
| A-89 | I.Ca | II-6 |
| A-90 | I.Cb | II-6 |
| A-91 | I.Cc | II-6 |
| A-92 | I.Ce | II-6 |
| A-93 | I.Cf | II-6 |
| A-94 | I.Da | II-6 |
| A-95 | I.Ea | II-6 |
| A-96 | I.Fa | II-6 |
| A-97 | I.Aa | II-7 |
| A-98 | I.Ab | II-7 |
| A-99 | I.Ac | II-7 |
| A-100 | I.Ba | II-7 |
| A-101 | I.Bb | II-7 |
| A-102 | I.Bc | II-7 |
| A-103 | I.Bd | II-7 |
| A-104 | I.Be | II-7 |
| A-105 | I.Ca | II-7 |
| A-106 | I.Cb | II-7 |
| A-107 | I.Cc | II-7 |
| A-108 | I.Ce | II-7 |
| A-109 | I.Cf | II-7 |
| A-110 | I.Da | II-7 |
| A-111 | I.Ea | II-7 |
| A-112 | I.Fa | II-7 |
| A-113 | I.Aa | II-8 |
| A-114 | I.Ab | II-8 |
| A-115 | I.Ac | II-8 |
| A-116 | I.Ba | II-8 |
| A-117 | I.Bb | II-8 |
| A-118 | I.Bc | II-8 |
| A-119 | I.Bd | II-8 |
| A-120 | I.Be | II-8 |
| A-121 | I.Ca | II-8 |
| A-122 | I.Cb | II-8 |
| A-123 | I.Cc | II-8 |
| A-124 | I.Ce | II-8 |
| A-125 | I.Cf | II-8 |
| A-126 | I.Da | II-8 |
| A-127 | I.Ea | II-8 |
| A-128 | I.Fa | II-8 |
| A-129 | I.Aa | II-9 |
| A-130 | I.Ab | II-9 |
| A-131 | I.Ac | II-9 |
| A-132 | I.Ba | II-9 |
| A-133 | I.Bb | II-9 |
| A-134 | I.Bc | II-9 |
| A-135 | I.Bd | II-9 |
| A-136 | I.Be | II-9 |
| A-137 | I.Ca | II-9 |
| A-138 | I.Cb | II-9 |

TABLE A-continued

| Line | Component 1 | Component 2 |
|---|---|---|
| A-139 | I.Cc | II-9 |
| A-140 | I.Ce | II-9 |
| A-141 | I.Cf | II-9 |
| A-142 | I.Da | II-9 |
| A-143 | I.Ea | II-9 |
| A-144 | I.Fa | II-9 |
| A-145 | I.Aa | II-10 |
| A-146 | I.Ab | II-10 |
| A-147 | I.Ac | II-10 |
| A-148 | I.Ba | II-10 |
| A-149 | I.Bb | II-10 |
| A-150 | I.Bc | II-10 |
| A-151 | I.Bd | II-10 |
| A-152 | I.Be | II-10 |
| A-153 | I.Ca | II-10 |
| A-154 | I.Cb | II-10 |
| A-155 | I.Cc | II-10 |
| A-156 | I.Ce | II-10 |
| A-157 | I.Cf | II-10 |
| A-158 | I.Da | II-10 |
| A-159 | I.Ea | II-10 |
| A-160 | I.Fa | II-10 |
| A-161 | I.Aa | II-11 |
| A-162 | I.Ab | II-11 |
| A-163 | I.Ac | II-11 |
| A-164 | I.Ba | II-11 |
| A-165 | I.Bb | II-11 |
| A-166 | I.Bc | II-11 |
| A-167 | I.Bd | II-11 |
| A-168 | I.Be | II-11 |
| A-169 | I.Ca | II-11 |
| A-170 | I.Cb | II-11 |
| A-171 | I.Cc | II-11 |
| A-172 | I.Ce | II-11 |
| A-173 | I.Cf | II-11 |
| A-174 | I.Da | II-11 |
| A-175 | I.Ea | II-11 |
| A-176 | I.Fa | II-11 |
| A-177 | I.Aa | II-12 |
| A-178 | I.Ab | II-12 |
| A-179 | I.Ac | II-12 |
| A-180 | I.Ba | II-12 |
| A-181 | I.Bb | II-12 |
| A-182 | I.Bc | II-12 |
| A-183 | I.Bd | II-12 |
| A-184 | I.Be | II-12 |
| A-185 | I.Ca | II-12 |
| A-186 | I.Cb | II-12 |
| A-187 | I.Cc | II-12 |
| A-188 | I.Ce | II-12 |
| A-189 | I.Cf | II-12 |
| A-190 | I.Da | II-12 |
| A-191 | I.Ea | II-12 |
| A-192 | I.Fa | II-12 |

The abovementioned active substances can also be used in the form of their agriculturally tolerated salts. Usually, alkali or alkaline-earth metal salts, such as sodium, potassium or calcium salts, are suitable for this purpose.

Among the above, it is particularly the mixtures mentioned in Table A which are preferred for controlling rust diseases in soya plants. The active substance combinations according to the invention comprise, besides an active substance of group (1), at least one active substance of the formula II. In addition, they may also comprise further fungicidally active components which can be admixed.

Thus, for example, each of the active substance combinations mentioned in Table A may comprise a third active substance selected from the following list:

A) azoles such as bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole; prochloraz, pefurazoate, imazalil, triflumizole, cyazofamid; benomyl, carbendazim, thiabendazole, fuberidazole; ethaboxam, etridiazole, hymexazole;

B) strobilurins such as azoxystrobin, dimoxystrobin, enestroburin, fluoxastrobin, kresoxim-methyl, metominostrobin, orysastrobin, picoxystrobin, pyraclostrobin, trifloxystrobin, or methyl (2-chloro-5-[1-(3-methylbenzyloxyimino)ethyl]benzyl)-carbamate, methyl (2-chloro-5-[1-(6-methylpyridin-2-ylmethoxyimino) ethyl]benzyl)-carbamate, methyl 2-(ortho-((2,5-dimethylphenyloxymethylene)phenyl)-3-methoxyacrylate;

C) carboxamides such as carboxin, benalaxyl, boscalid, fenhexamid, flutolanil, furametpyr, mepronil, metalaxyl, mefenoxam, ofurace, oxadixyl, oxycarboxin, penthiopyrad, thifluzamide, tiadinil, N-(4'-bromobiphenyl-2-yl)4-difluoromethyl-2-methylthiazole-5-carboxamide, N-(4'-trifluoromethylbiphenyl-2-yl)4-difluoromethyl-2-methylthiazole-5-carboxamide, N-(4'-chloro-3'-fluorobiphenyl-2-yl)4-difluoromethyl-2-methylthiazole-5-carboxamide, N-(3',4'-dichloro-4-fluorobiphenyl-2-yl) 3-difluoromethyl-1-methylpyrazole-4-carboxamide, N-(3',4'-dichloro-5-fluorobiphenyl-2-yl)3-difluoromethyl-1-methylpyrazole-4-carboxamide; N-(2-cyanophenyl) 3,4-dichloroisothiazole-5-carboxamide; dimethomorph, flumorph; flumetover, fluopicolide (picobenzamide), zoxamide; carpropamid, diclocymet, mandipropamid; N-(2-{4-[3-(4-chlorophenyl)prop-2-ynyloxy]-3-methoxyphenyl}ethyl)-2-methanesulfonylamino-3-methylbutyramide, N-(2-{4-[3-(4-chlorophenyl)prop-2-ynyloxy]-3-methoxyphenyl}ethyl)-2-ethanesulfonylamino-3-methylbutyramide;

D) heterocyclic compounds such as fluazinam, pyrifenox; bupirimate, cyprodinil, fenarimol, ferimzone, mepanipyrim, nuarimol, pyrimethanil; triforine; fenpiclonil, fludioxonil; aldimorph, dodemorph, fenpropimorph, tridemorph; fenpropidin, iprodione, procymidone, vinclozolin; famoxadone, fenamidone, octhilinone, probenazole; amisulbrom, anilazin, diclomezine, pyroquilon, proquinazid, tricyclazole; 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one; acibenzolar-S-methyl, captafol, captan, dazomet, folpet, fenoxanil, quinoxyfen; 3-[5-(4-chlorophenyl)-2,3-dimethylisoxazolidin-3-yl]pyridine;

E) carbamates such as mancozeb, maneb, metam, metiram, ferbam, propineb, thiram, zineb, ziram; diethofencarb, iprovalicarb, flubenthiavalicarb, propamocarb; methyl 3-(4-chlorophenyl)-3-(2-isopropoxycarbonylamino-3-methylbutyrylamino)-propanoate;

and

F) other active substances, such as guanidines: dodine, iminoctadine, guazatine; antibiotics: kasugamycin, streptomycin, polyoxine, validamycin A; nitrophenyl derivatives: binapacryl, dinocap, dinobuton; sulfur-containing heterocyclyl compounds: dithianon, isoprothiolane; organometallic compounds: fentin salts such as fentin-acetate; organophosphorus compounds: edifenphos, iprobenfos, fosetyl, fosetyl-aluminum, phosphorous acid and its salts, pyrazophos, tolclofos-methyl; organochlorine compounds: chlorothalonil, dichlofluanid, flusulfamide, hexachlorobenzene, phthalide, pencycuron, quintozene, thiophanate-methyl, tolylfluanid; inorganic active substances: Bordeaux mixture, copper acetate, copper hydroxide, copper oxychloride, basic copper sulfate, sulfur; others: cyflufenamid, cymoxanil, dimethirimol, ethirimol, furalaxyl, metrafenone, spiroxamine N-(cyclopropylmethoxyimino-(6-difluoromethoxy-2,3-difluorophenyl)methyl)-2-phenylacetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine and N'-(5-difluoromethyl-2-methyl-4-(3-trimethylsilanylpropoxy)phenyl)-N-ethyl-N-methylformamidine; growth retardants: prohexadione and its salts, trinexapac-ethyl, chlormequat, mepiquat-chloride and diflufenzopyr.

The synergistic effect is particularly pronounced when the active substances in the active substance combinations according to the invention are present in certain weight ratios. However, the weight ratios of the active substances in the active substance combinations can be varied within a relatively wide range.

The mixing ratios are based on weight ratios. The ratio is to be understood as meaning active substance of group (1): mixing partner of the formula II.

Depending on the desired effects and the specific active substances I and II, the weight ratios of the herbicides I and active substances II are generally from 100:1 to 1:1000, preferably 20:1 to 1:500, preferably 20:1 to 1:200, in particular 10:1 to 1:200, or 10:1 to 1:20.

If desired, the further active components are admixed to the compound of the formula II in a ratio of 50:1 to 1:50, preferably 20:1 to 1:20.

In any case, the mixing ratio is to be selected in such a way that a synergistic mixture is obtained. The mixing ratios between the compound (I) and a compound of the formula II may also vary between the individual compounds of one group.

The active substance combinations according to the invention have very good fungicidal properties and can be employed for controlling phytopathogenic fungi such as Plasmodiophoromycetes, Oomycetes, Chytridiomycetes, Zygomycetes, Ascomycetes, Basidiomycetes, Deuteromycetes and the like.

Examples which may be mentioned, but not by limitation, of some pathogens of fungal and bacterial diseases which come under the abovementioned general terms are:

Diseases caused by powdery mildew pathogens, such as, for example, *Blumeria* species such as, for example, *Blumeria graminis*; *Podosphaera* species such as, for example, *Podosphaera leucotricha*; *Sphaerotheca* species such as, for example, *Sphaerotheca fuliginea*; *Uncinula* species such as, for example, *Uncinula necator*;

Diseases caused by rust pathogens such as, for example, *Gymnosporangium* species such as, for example, *Gymnosporangium sabinae*; *Hemileia* species such as, for example, *Hemileia vastatrix*;

*Phakopsora* species such as, for example, *Phakopsora pachyrhizi* and *Phakopsora meibomiae*; *Puccinia* species such as, for example, *Puccinia recondita*;

Uromyces species such as, for example, *Uromyces appendiculatus*;

Diseases caused by pathogens from the Oomycetae group such as, for example, *Bremia* species such as, for example, *Bremia lactucae*; *Peronospora* species such as, for example, *Peronospora pisi* or *P. brassicae*;

*Phytophthora* species such as, for example, *Phytophthora infestans*;

*Plasmopara* species such as, for example, *Plasmopara viticola*;

*Pseudoperonospora* species such as, for example, *Pseudoperonospora humuli* or *Pseudoperonospora cubensis*; *Pythium* species such as, for example, *Pythium ultimum*;

Leaf spot diseases and leaf wilts caused by, for example, *Alternaria* species such as, for example, *Alternaria solani*;

*Cercospora* species such as, for example, *Cercospora beticola*; *Cladosporum* species such as, for example, *Cladosporium cucumerinum*;

*Cochliobolus* species such as, for example, *Cochliobolus sativus* (coonidial form: *Drechslera*, syn: *Helminthosporium*);

*Colletotrichum* species such as, for example, *Colletotrichum lindemuthanium*;

*Cycloconium* species such as, for example, *Cycloconium oleaginum*; *Diaporthe* species such as, for example, *Diaporthe citri*; *Elsinoe* species such as, for example, *Elsinoe fawcettii*;

*Gloeosporium* species such as, for example, *Gloeosporium laeticolor*;

*Glomerella* species such as, for example, *Glomerella cingulata*;

*Guignardia* species such as, for example, *Guignardia bidwelli*; *Leptosphaeria* species such as, for example, *Leptosphaeria maculans*;

*Magnaporthe* species such as, for example, *Magnaporthe grisea*; *Mycosphaerella* species such as, for example, *Mycosphaerelle graminicola*; *Phaeosphaeria* species such as, for example, *Phaeosphaeria nodorum*; *Pyrenophora* species such as, for example, *Pyrenophora teres*; *Ramularia* species such as, for example, *Ramularia collo-cygni*; *Rhynchosporium* species such as, for example, *Rhynchosporium secalis*;

*Septoria* species such as, for example, *Septoria apii*; *Typhula* species such as, for example, *Typhula incarnata*; *Venturia* species such as, for example, *Venturia inaequalis*;

Root and stem diseases caused by, for example,

*Corticium* species such as, for example, *Corticium graminearum*;

*Fusarium* species such as, for example, *Fusarium oxysporum*;

*Gaeumannomyces* species such as, for example, *Gaeumannomyces graminis*;

*Rhizoctonia* species such as, for example, *Rhizoctonia solani*; *Tapesia* species such as, for example, *Tapesia acuformis*;

*Thielaviopsis* species such as, for example, *Thielaviopsis basicola*;

Ear and panicle diseases (including maize cobs), caused by, for example, *Alternaria* species such as, for example, *Alternaria* spp.; *Aspergillus* species such as, for example, *Aspergillus flavus*;

*Cladosporium* species such as, for example, *Cladosporium* spp.; *Claviceps* species such as, for example, *Claviceps purpurea*;

*Fusarium* species such as, for example, *Fusarium culmorum*; *Gibberella* species such as, for example, *Gibberella zeae*; *Monographella* species such as, for example, *Monographella nivalis*;

Diseases caused by smuts such as, for example, *Sphacelotheca* species such as, for example, *Sphacelotheca reiliana*; *Tilletia* species such as, for example, *Tilletia caries*; Urocystis species such as, for example, *Urocystis occulta*; *Ustilago* species such as, for example, *Ustilago nuda*;

Fruit rot caused by, for example, *Aspergillus* species such as, for example, *Aspergillus flavus; Botrytis* species such as, for example, *Botrytis cinerea;*

*Penicillium* species such as, for example, *Penicillium expansum;*

*Sclerotinia* species such as, for example, *Sclerotinia sclerotiorum; Verticilium* species such as, for example, *Verticilium alboatrum;*

Seed- and soil-borne rot and wilts, and seedling diseases, caused by, for example, *Fusarium* species such as, for example, *Fusarium culmorum;*

*Phytophthora* species such as, for example, *Phytophthora cactorum; Pythium* species such as, for example, *Pythium ultimum; Rhizoctonia* species such as, for example, *Rhizoctonia solani; Sclerotium* species such as, for example, *Sclerotium rolfsii;*

Cankers, galls and witches' broom disease, caused by, for example, *Nectria* species such as, for example, *Nectria galligena;*

Wilts caused by, for example, *Monilinia* species such as, for example, *Monilinia laxa;*

Deformations of leaves, flowers and fruits, caused by, for example, *Taphrina* species such as, for example, *Taphrina deformans;*

Degenerative diseases of woody species, caused by, for example, Esca species such as, for example, *Phaemoniella clamydospora;*

Diseases of inflorescences and seeds, caused by, for example, *Botrytis* species such as, for example, *Botrytis cinerea;*

Diseases of the plant tubers, caused by, for example, *Rhizoctonia* species such as, for example, *Rhizoctonia solani;*

Diseases caused by bacterial pathogens such as, for example, *Xanthomonas* species such as, for example, *Xanthomonas campestris* pv. *oryzae; Pseudomonas* species such as, for example, *Pseudomonas syringae* pv. *lachrymans; Erwinia* species such as, for example, *Erwinia amylovora;*

The following diseases of soybeans can preferably be controlled:

Fungal diseases on leaves, stems, pods and seeds caused by, for example, *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora cassiicola*)

Fungal diseases on roots and the stem base caused by, for example, black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active substance combinations according to the invention are particularly suitable for controlling diseases which are caused by rust pathogens, such as, for example, *Phakopsora* species, such as, for example, *Phakopsora pachyrhizi* and *Phakopsora meibomiae.*

The following diseases of soybeans can be controlled by preference: fungal diseases on leaves, stems, pods and seeds, caused by rust (*Phakopsora pachyrhizi* and *Phakopsora meibomiae*). Especially preferred is the control of *Phakopsora pachyrhizi*.

The good tolerance, by plants, of the active substance combinations at the concentrations required for controlling plant diseases permits the treatment of intact plants (aerial plant parts and roots), of vegetative propagation material and seed, and of the soil. The active substance combinations according to the invention can be employed for foliar application or else as seed-dressing materials.

A large part of the crop plant damage caused by phytopathogenic fungi is the result of the seed already being attacked during storage and after the seed has been introduced into the soil, and during and immediately after germination of the plants. This phase is particularly critical since the roots and shoots of the growing plant are particularly sensitive and even a minor degree of damage can lead to the death of the entire plant. There is therefore in particular a great interest in protecting the seed and the germinating plant by using suitable compositions.

The control of phytopathogenic fungi which damage plants after emergence is mainly accomplished by treating the soil and the aerial plant parts with plant protection products. As a result of reservations regarding a potential effect of the plant protection products on the environment and the health of humans and animals, attempts are being made to reduce the amount of the active substances which are applied.

The control of phytopathogenic fungi by the treatment of the seed of plants has long been known and is the subject of continuous improvement. However, the treatment of seed leads to a series of problems which cannot always be solved satisfactorily. Thus, it is desirable to develop methods of protecting the seed and the germinating plant which do away with, or at least substantially reduce, the additional application of crop protection products after sowing or after the emergence of the plants. Moreover it is desirable to optimize the amount of the active substance employed in such a way that the seed and the germinating plant are protected in the best possible manner against attack by phytopathogenic fungi without the plant itself being damaged by the active substance employed. In particular, methods for the treatment of seed should also incorporate the intrinsic fungicidal properties of transgenic plants in order to achieve an optimal protection of the seed and of the germinating plant while applying the minimum amount of plant protection products.

The present invention therefore particularly also relates to a method of protecting seed and germinating plants against attack by phytopathogenic fungi, by treating the seed with a composition according to the invention.

The invention also relates to the use of the compositions according to the invention for the treatment of seed for protecting the seed and the germinating plant from phytopathogenic fungi.

Furthermore, the invention relates to seed which has been treated with a composition according to the invention as protection from phytopathogenic fungi. One of the advantages of the present invention is that, as the result of the specific systemic properties of the compositions according to the invention, the treatment of the seed with these compositions protects not only the seed itself, but also, after emergence, the plants which the seeds give rise to, against phytopathogenic fungi. In this manner, the immediate treatment of the crop at the point in time of sowing or shortly thereafter can be dispensed with.

Equally, it can be seen as advantageous that the mixtures according to the invention can also be employed in particular in transgenic seed.

The compositions according to the invention are suitable for the protection of seed of any plant variety which is employed in agriculture, in the greenhouse, in forests or in horticulture. In particular, this takes the form of seed of cereals (such as wheat, barley, rye, sorghum/millet and oats), maize, cotton, soybeans, rice, potatoes, sunflower, bean, coffee, beet (for example sugar beet and fodder beet), peanut, vegetables (such as tomato, cucumber, onions and lettuce), turf and ornamentals. The treatment of the seed of cereals (such as wheat, barley, rye and oats), maize and rice is of particular importance. Also of particular importance is the treatment of soybean seed.

For the purposes of the present invention, the composition according to the invention is applied to the seed on its own or in a suitable formulation. Preferably, the seed is treated in a state in which it is sufficiently stable to avoid damage upon the treatment. In general, the treatment of the seed can be effected at any point in time between harvesting and sowing. Usually, seed will be used which has been separated from the plant and freed from cobs, husks, stems, hull, fiber or pulp. Thus, for example, seed can be used which has been harvested, cleaned and dried down to a moisture content of less than 15% by weight. Alternatively, it is also possible to use seed which, after drying, has been treated for example with water and then redried.

In general, care must be taken when treating the seed that the amount of the composition according to the invention and/or of further additives applied to the seed is selected in such a way that the germination of the seed is not adversely affected, or that the plant which the seed gives rise to is not damaged. This must be considered in particular in the case of active substances which can exhibit phytotoxic effects at certain application rates.

The compositions according to the invention can be applied directly, that is to say without comprising further components and without having been diluted. As a rule, it is preferred to apply the compositions to the seed in the form of a suitable formulation. Suitable formulations and methods for the treatment of seed are known to the skilled worker and are described for example in the following documents: U.S. Pat. No. 4,272,417, U.S. Pat. Nos. 4,245,432, 4,808,430, 5,876, 739, US 2003/0176428, WO 2002/080675, WO 2002/ 028186.

The active substance combinations according to the invention are also suitable for increasing the yield. Moreover, they show a low degree of toxicity and are well tolerated by plants.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention of the plants and plant parts (including seed) with the active substance combinations is accomplished directly or by acting on their surroundings, environment or storage space, using the customary treatment methods, for example by dipping, spraying, vaporizing, fogging, scattering, brushing on and, in the case of propagation material, in particular seeds, furthermore by coating with one or more coats. In this context, the active substance combinations can be prepared prior to the treatment by mixing the individual active substances and are thus employed as a mixture. Or else, the treatment is effected in succession by firstly employing a herbicide of group (1) followed by the treatment with an active substance of the formula II. However, it is also possible first to treat the plants or plant parts (including seed) with an active substance of the formula II and to follow with treatment with a herbicide of group (1). In particular, it is also possible to coat seed first with one or more active substances of the formula II in one or more coats and to spray the resulting plants with a herbicide of group (1) only when an infection has emerged (for example seed of soybean or maize is first treated with one of the compounds of Table 1, whereupon a foliar application with glyphosate is effected at a later point in time; or seed of oilseed rape is first treated with fluquinconazole or carboxin, whereupon a foliar application with glufosinate is effected at a later point in time).

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention.

Depending on the plant species or plant cultivars, their location and growth conditions (soils, climate, vegetation period, nutrition), the treatment according to the invention may also result in more pronounced superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processibility of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparts particular advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processibility of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active substances. Examples of transgenic plants which may be mentioned are the important crop plants, such as cereals (wheat, rice), maize, soybeans, potatoes, cotton, oilseed rape and also fruit plants (with the fruits apples, pears, citrus fruits and grapes), and particular emphasis is given to maize, soybeans, potatoes, cotton and oilseed rape, in particular soybeans. Traits that are emphasized in particular are increased defense of the plants against insects as the result of toxins formed in the plants, in particular those formed in the plants by the genetic material from *Bacillus thuringiensis* (for example by the genes CryIA (a), CryIA(b), CryIA(c), CryIIA, CryIHA, CryDIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active substances, for example imidazolinones, sulfonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soybean varieties and potato varieties which are sold under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance to glyphosates, for example maize, cotton, soybeans), Liberty Link® (tolerance to phosphinotricin, for example oilseed rape), EMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant varieties which are developed in the future, or will be commercially available in the future, and which have these genetic traits or genetic traits yet to be developed.

Depending on their particular physical and/or chemical properties, the active substance combinations according to the invention can be converted into the customary formulations, such as solutions, emulsions, suspensions, powders, dusts, foams, pastes, soluble powders, granules, aerosols, suspoemulsion concentrates, natural and synthetic materials which are impregnated with active substance, and microencapsulations in polymeric substances and in coating compositions for seed, and ULV cold- and warm-fogging formulations.

These formulations are prepared in a known manner, for example by mixing the active substances, or the active substance combinations, with extenders, that is liquid solvents, pressurized liquefied gases and/or solid carriers, if appropriate using surfactants, that is emulsifiers and/or dispersants and/or foam formers.

If water is used as extender, it is also possible for example to use organic solvents as cosolvents. Liquid solvents which are suitable are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones, such as acetone, methyl ethyl ketone, methyl isobutyl ketone or cyclohexanone, strongly polar solvents such as dimethylformamide and dimethyl sulfoxide, and water.

Liquefied gaseous extenders or carriers are understood as meaning those liquids which are gaseous at normal temperature and under atmospheric pressure, for example aerosol propellants such as butane, propane, nitrogen and carbon dioxide.

Solid carriers which are suitable are: for example ammonium salts and ground natural minerals such as kaolins, clays, talc, chalk, quartz, attapuigite, montmorillonite or diatomaceous earth, and ground synthetic minerals, such as highly disperse silica, alumina and silicates. Solid carriers for granules which are suitable are: for example crushed and fractionated natural rocks such as calcite, marble, pumice, sepiolite, dolomite and synthetic granules of organic and inorganic meals, and granules of organic material such as sawdust, coconut shells, maize cobs and tobacco stalks. Suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates and protein hydrolyzates. Dispersants which are suitable are: for example lignin-sulfite waste liquors and methylcellulose.

Adhesives such as carboxymethylcellulose, natural and synthetic polymers in the form of powders, granules or latices such as gum arabic, polyvinyl alcohol, polyvinyl acetate, and natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide, Prussian blue, and organic dyestuffs such as alizarin, azo and metal phthalocyanin dyestuffs and trace nutrients such as salts of iron, manganese, boron, copper, cobalt, molybdenum and zinc. The active substance content of the use forms prepared from the commercially available formulations can vary within wide limits. The active substance concentration of the use forms for controlling animal pests such as insects and acarids can range from 0.0000001 to 95% by weight of active substance, preferably between 0.0001 and 1% by weight. The application is accomplished in a customary manner adapted to the use forms.

The formulations for controlling undesirable phytopathogenic fungi generally comprise between 0.1 and 95% by weight of active substances, preferably between 0.5 and 90%.

The active substance combinations according to the invention can be applied as such, in the form of their formulations or the use forms prepared therefrom, such as ready-to-use solutions, emulsifiable concentrates, emulsions, suspensions, wettable powders, soluble powders, dusts and granules. They are applied in a customary manner, for example by drenching, trickle irrigation, spraying, atomizing, scattering, dusting, foaming, painting on, brushing on, by the dry seed treatment, by seed treatment with a solution, a water-soluble powder or a water-dispersible powder, by encrusting and the like.

In commercially available formulations and in the use forms prepared from these formulations, the active substance combinations according to the invention can be present as a mixture with other active substances such as insecticides, attractants, sterilants, bactericides, acaricides, nematicides, fungicides, growth regulators or herbicides.

When using the active substance combinations according to the invention, the application rates can be varied within a substantial range, depending on the type of application. In the treatment of plant parts, the application rates of active substance combination are generally between 0.1 and 10 000 g/ha, preferably between 10 and 1000 g/ha. In the treatment of seed, the application rates of active substance combination are generally between 0.001 and 50 g per kilogram of seed, preferably between 0.01 and 10 g per kilogram of seed. In the treatment of the soil, the application rates of active substance combination are generally between 0.1 and 10 000 g/ha, preferably between 1 and 5000 g/ha.

The active substance combinations can be employed as such, in the form of concentrates or generally customary formulations such as powders, granules, solutions, suspensions, emulsions or pastes.

The abovementioned formulations can be prepared in a manner known per se, for example by mixing the active substances with at least one solvent or diluent, emulsifier, dispersant and/or binder or fixative, water repellant, if appropriate desiccants and UV stabilizers and, if appropriate, colorants and pigments and further processing auxiliaries.

The good fungicidal activity of the active substance combinations according to the invention can be seen from the examples which follow.

USE EXAMPLES

Greenhouse

The active substances, separately or individually, were prepared as a stock solution, using 25 mg of active substance, which was made up to 10 ml with a mixture of acetone and/or DMSO and the emulsifier Uniperol® EL (wetter based on ethoxylated alkylphenols, with emulsifying and disputing activity) in the volumetric solvent/emulsifier ratio of 99 to 1. Then, the mixtures were made up to 100 ml with water. This stock solution was diluted with the above-described solvent/emulsifier/water mixture to give the active substance concentration stated below. As an alternative, the active substances were used as a commercially available ready mix and made up to the active substance concentration stated with water.

The visually determined values for the percentage of affected leaf area were converted into efficacies as % of the untreated control:

The efficacy (E) is calculated as follows, using Abbot's formula:

$$E = (1 - \alpha/\beta) \cdot 100$$

α corresponds to the fungal disease level of the treated plants in % and

β corresponds to the fungal disease level of the untreated (control) plants in %

At an efficacy of 0 the disease level of the treated plants corresponds to that of the untreated control plants; at an efficacy of 100, the treated plants are not diseased.

The expected efficacies for active substance combinations were determined using the Colby formula (Colby, S. R. (Calculating synergistic and antagonistic responses of herbicide Combinations", Weeds, 15, p. 20-22, 1967) and compared with the observed efficacies.

Colby Formula:

$$E = x + y - x \cdot y / 100$$

E expected efficacy, expressed in % of the untreated control, when employing the mixture of the active substances A and B at the concentrations a and b x efficacy, expressed in % of the untreated control, when employing active substance A at concentration a y efficacy, expressed in % of the untreated control, when employing active substance B at concentration b

Use Example 1

Activity Against Late Blight on Tomatoes, Caused by *Phytophthora infestans*, when Treated Protectively Leaves of pot-grown tomato plants were sprayed to runoff point with an aqueous suspension in the active substance concentration stated below. On the next day, the leaves were inoculated with an aqueous sporangia suspension of *Phytophthora infestans*. Thereafter, the plants were placed into a water-vapor-saturated chamber at temperatures of between 18 and 20° C. After 6 days, the late blight disease on the untreated, but infected, control plants had developed to such an extent that it was possible to determine the disease level visually in %.

| No. | Active substance | Conc. [ppm] | Ratio | Observed effect (%) | Calculated Colby effect (%) |
|---|---|---|---|---|---|
| 1 | — (Control) | — | | 0 (disease level 90%) | |
| 2 | Dimetheneamid-P (I.Ea) | 0.063 | | 22 | |
| 3 | Paraquat (I.Fa) | 0.25 | | 0 | |
| 4 | | 0.063 | | 0 | |
| 5 | II-8 | 4 | | 22 | |
| 6 | II-10 | 16 | | 0 | |
| 7 | I.Ea + II-8 | 0.063 + 4 | 1:63 | 89 | 40 |
| 8 | I.Fa + II-8 | 0.063 + 4 | 1:63 | 67 | 22 |
| 9 | I.Fa + II-10 | 0.25 + 16 | 1:63 | 22 | 0 |

Use Example 2

Activity when used Protectively for 1 Day Against Gray Mold on *capsicum* Leaves, Caused by *Botrytis cinerea*

*Capsicum* seedlings were allowed to develop 2-3 leaves properly and were then sprayed to runoff point with an aqueous suspension of the active substance concentration stated below. On the next day, the treated plants were inoculated with a spore suspension of *Botrytis cinerea* in a 2% strength Biomalz solution. Thereafter, the test plants were placed into a controlled-environment cabinet at 22 to 24° C. in the dark and with high atmospheric humidity. After 5 days, it was possible to visually determine the extent of the fungal disease level on the leaves in %.

| No. | Active substance | Conc. [ppm] | Ratio | Observed effect (%) | Calculated Colby effect (%) |
|---|---|---|---|---|---|
| 10 | — (Control) | — | | 0 (disease level 90%) | |
| 11 | Dimetheneamid-P (I.Ea) | 0.25 | | 0 | |
| 12 | Paraquat (I.Fa) | 0.25 | | 0 | |
| 13 | II-6 | 16 | | 0 | |
| 14 | II-10 | 16 | | 0 | |
| 15 | I.Ea + II-10 | 0.25 + 16 | 1:63 | 22 | 0 |
| 16 | I.Fa + II-6 | 0.25 + 16 | 1:63 | 50 | 0 |
| 17 | I.Fa + II-10 | 0.25 + 16 | 1:63 | 33 | 0 |

Use Example 3

Protective Activity Against *Puccinia recondita* on Wheat (Leaf Rust of Wheat)

Leaves of pot-grown wheat seedlings were sprayed to run-off point with an aqueous suspension at the active substance concentration stated below. On the next day, the treated plants were inoculated with a spore suspension of leaf rust of wheat (*Puccinia recondita*). Thereafter, the plants were placed for 24 hours into a chamber with high atmospheric humidity (90 to 95%) at 20 to 22° C. During this time, the spores germinated, and the germ tubes penetrated the leaf tissue. On the next day, the test plants were returned to the greenhouse and grown on for a further 7 days at temperatures of between 20 and 22° C. and a relative atmospheric humidity of 65 to 70%. Then, the extent of the development of the rust fungus on the leaves was determined visually.

| No. | Active substance | Conc. [ppm] | Ratio | Observed effect (%) | Calculated Colby effect (%) |
|---|---|---|---|---|---|
| 18 | — (Control) | — | | 0 (disease level 90%) | |
| 19 | Glyphosate (I.Aa) | 0.063 | | 0 | |
| 20 | II-6 | 4 | | 0 | |
| 21 | I.Aa + II-6 | 0.063 + 4 | 1:63 | 22 | 0 |

Use Example 4

Curative Activity Against Leaf Rust of Wheat, Caused by *Puccinia recondita*

Leaves of pot-grown wheat seedlings were inoculated with a spore suspension of leaf rust (*Puccinia recondita*). Then, the pots were placed for 24 hours into a chamber with high atmospheric humidity (90 to 95%) at 20 to 22° C. During this time, the spores germinated, and the germ tubes penetrated the leaf tissue. On the next day, the infected plants were sprayed to runoff point with the above-described active substance solution at the active substance concentration stated below. After the spray coating had dried on, the test plants were grown in the greenhouse at temperatures of between 20 and 22° C. and a relative atmospheric humidity of 65 to 70%. Then, the extent of the development of the rust fungus on the leaves was determined visually.

| No. | Active substance | Conc. [ppm] | Ratio | Observed effect (%) | Calculated Colby effect (%) |
|---|---|---|---|---|---|
| 22 | — (Control) | — | | 0 (disease level 90%) | |
| 23 | Glyphosate (I.Aa) | 0.063 | | 0 | |
| 24 | II-6 | 4 | | 0 | |
| 25 | I.Aa + II-6 | 0.063 + 4 | 1:63 | 83 | 0 |

Use Example 5

Activity when Used Protectively for 1 Day Against Barley Net Blotch Disease Caused by *Pyrenophora teres*

Leaves of pot-grown barley seedlings were sprayed to run-off point with aqueous suspension at the active substance concentration stated below. 24 hours after the spray coating had dried on, the test plants were inoculated with an aqueous spore suspension of *Pyrenophora* [syn. *Drechslera*] teres, the pathogen causing net blotch disease. Thereafter, the test plants were placed in the greenhouse at temperatures of between 20 and 24° C. and a relative atmospheric humidity of 95 to 100%. After 6 days, the extent of the disease development was determined visually as % disease of the total leaf area.

| No. | Active substance | Conc. [ppm] | Ratio | Observed effect (%) | Calculated Colby effect (%) |
|---|---|---|---|---|---|
| 26 | — (Control) | — | | 0 (disease level 90%) | |
| 27 | Sethoxydim (I.Bc) | 0.25 | | 0 | |
| 28 | II-10 | 16 | | 0 | |
| 29 | I.Bc + II-10 | 0.25 + 16 | 1:63 | 56 | 0 |

Use Example 6

Curative Activity Against Soybean Rust Caused by *Phakopsora pachyrhizi*

Leaves of pot-grown soybean seedlings were inoculated with a spore suspension of soybean rust (*Phakopsora pachyrhizi*). Then, the pots were placed for 24 hours into a chamber with high atmospheric humidity (90 to 95%) at 23 to 27° C. During this time, the spores germinated, and the germ tubes penetrated the leaf tissue. After one day, the infected plants were sprayed to runoff point with the above-described active substance solution at the active substance concentration stated below. After the spray coating had dried on, the test plants were grown in the greenhouse at temperatures of between 23 and 27° C. and a relative atmospheric humidity of 60 to 80%. Then, the extent of the development of the rust fungus on the leaves was determined.

| No. | Active substance | Conc. [ppm] | Ratio | Observed effect (%) | Calculated Colby effect (%) |
|---|---|---|---|---|---|
| 30 | — (Control) | — | | 0 (disease level 90%) | |

-continued

| No. | Active substance | Conc. [ppm] | Ratio | Observed effect (%) | Calculated Colby effect (%) |
|---|---|---|---|---|---|
| 31 | Paraquat (I.Fa) | 0.25 | | 0 | |
| 32 | II-10 | 16 | | 0 | |
| 33 | I.Fa + II-10 | 0.25 + 16 | 1:63 | 33 | 0 |

Use Example 7

Activity Against Downy Mildew of Grapevine Caused by *Plasmopara viticola*

Leaves of pot-grown grapevines were sprayed to runoff point with aqueous suspension at the active substance concentration stated below. On the next day, the abaxial sides of the leaves were inoculated with an aqueous sporangia suspension of *Plasmopara viticola*. Then, the grapevines were placed first for 24 hours into a water-vapor-saturated chamber at 24° C. and then for 5 days in the greenhouse at temperatures of between 20 and 30° C. After this time, the plants were returned into a humid chamber for 16 hours in order to accelerate the eruption of the sporangiophores. Then, the extent of the disease development on the abaxial sides of the leaves was determined visually.

| No. | Active substance | Conc. [ppm] | Ratio | Observed effect (%) | Calculated Colby effect (%) |
|---|---|---|---|---|---|
| 34 | — (Control) | — | | 0 (disease level 90%) | |
| 35 | Glyphosate (I.Aa) | 0.016 | | 0 | |
| 36 | Glufosinate (I.Ab) | 0.25 | | 0 | |
| 37 | | 0.063 | | 0 | |
| 38 | Cycloxydim (I.Ba) | 0.063 | | 0 | |
| 39 | Sethoxydim (I.Bc) | 0.25 | | 0 | |
| 40 | Imazapyr (I.Ca) | 0.063 | | 0 | |
| 41 | Imazethapyr (I.Cb) | 0.25 | | 0 | |
| 42 | Imazaquin (I.Cc) | 0.25 | | 0 | |
| 43 | Imazapic (I.Cd) | 0.25 | | 0 | |
| 44 | | 0.063 | | 0 | |
| 45 | Pendimethalin (I.Da) | 0.25 | | 0 | |
| 46 | Dimethenamid-P (I.Ea) | 0.016 | | 0 | |
| 47 | II-6 | 16 | | 44 | |
| 48 | II-7 | 4 | | 22 | |
| 49 | | 1 | | 0 | |
| 50 | II-8 | 1 | | 33 | |
| 51 | II-10 | 16 | | 44 | |
| 52 | | 4 | | 0 | |
| 53 | I.Aa + II-7 | 0.016 + 1 | 1:63 | 33 | 0 |
| 54 | I.Aa + II-10 | 0.25 + 16 | 1:63 | 72 | 44 |
| 55 | I.Ab + II-7 | 0.063 + 4 | 1:63 | 89 | 22 |
| 56 | I.Ab + II-10 | 0.25 + 16 | 1:63 | 89 | 44 |
| 57 | I.Ba + II-10 | 0.063 + 4 | 1:63 | 22 | 0 |
| 58 | I.Bc + II-7 | 0.25 + 16 | 1:63 | 100 | 78 |
| 59 | I.Ca + II-7 | 0.063 + 4 | 1:63 | 67 | 22 |
| 60 | I.Cb + II-6 | 0.25 + 16 | 1:63 | 67 | 44 |
| 61 | I.Cb + II-10 | 0.25 + 16 | 1:63 | 72 | 44 |
| 62 | I.Cc + II-10 | 0.25 + 16 | 1:63 | 67 | 44 |
| 63 | I.Cd + II-7 | 0.063 + 4 | 1:63 | 83 | 22 |
| 64 | I.Cd + II-10 | 0.25 + 16 | 1:63 | 92 | 44 |
| 65 | I.Da + II-7 | 0.25 + 16 | 1:63 | 100 | 78 |
| 66 | I.Ea + II-8 | 0.25 + 16 | 1:63 | 83 | 33 |

Microtest

The active substances were formulated separately as a stock solution having a concentration of 10 000 ppm in DMSO.

Use Example 8

Activity in the Microtiter Test Against the Pathogen Causing Late Blight Disease, *Phytophthora infestans* (Phytin)

The stock solution is pipetted into a microtiter plate (MTP) and diluted with an aqueous pea-juice-based fungal nutrient medium to the active substance concentration stated. Thereafter, an aqueous zoospore suspension of *Phytophthora infestans* was added. The plates were placed into a water-vapor-saturated chamber at temperatures of 18° C. The MTPs were measured on day 7 post-inoculation at 405 nm, using an absorption photometer.

The parameters measured were compared with the growth of the active-substance-free control variant and the fungus- and active-substance-free blank value in order to determine the relative growth in % of the pathogens in the individual active substances.

| No. | Active substance | Conc. [ppm] | Ratio | Observed effect (%) | Calculated Colby effect (%) |
|---|---|---|---|---|---|
| 67 | II-6 | 16 | | 25 | |
| 68 | II-7 | 1 | | 7 | |
| 69 | II-8 | 4 | | 1 | |
| 70 | II-10 | 0.25 | | 10 | |
| 71 | Pendimethalin | 63 | | 38 | |
| 72 | (I.Da) | 16 | | 29 | |
| 73 | | 4 | | 16 | |
| 74 | | 1 | | 7 | |
| 75 | Glyphosate (I.Aa) | 16 | | 13 | |
| 76 | | 4 | | 1 | |
| 77 | | 1 | | 4 | |
| 78 | Glufosinate (I.Ab) | 16 | | 20 | |
| 79 | | 4 | | 12 | |
| 80 | | 1 | | 3 | |
| 81 | Cycloxydim (I.Ba) | 16 | | 13 | |
| 82 | | 4 | | 5 | |
| 83 | | 1 | | 9 | |
| 84 | Imazapyr (I.Ca) | 16 | | 8 | |
| 85 | | 4 | | 9 | |
| 86 | | 1 | | 1 | |
| 87 | Imazethapyr (I.Cb) | 16 | | 9 | |
| 88 | | 4 | | 8 | |
| 89 | | 1 | | 3 | |
| 90 | Imazaquin (I.Cc) | 16 | | 23 | |
| 91 | | 4 | | 11 | |
| 92 | | 1 | | 8 | |
| 93 | Imazapic (I.Cd) | 16 | | 12 | |
| 94 | | 4 | | 4 | |
| 95 | | 1 | | 4 | |
| 96 | Sethoxydim (I.Bc) | 16 | | 14 | |
| 97 | | 4 | | 5 | |
| 98 | | 1 | | 2 | |
| 99 | Paraquat (I.Fa) | 16 | | 7 | |
| 100 | | 4 | | 5 | |
| 101 | | 1 | | 4 | |
| 102 | I.Da + II-6 | 63 + 16 | 4:1 | 92 | 54 |
| 103 | I.Aa + II-7 | 4 + 1 | 4:1 | 94 | 8 |
| 104 | I.Ab + II-7 | 4 + 1 | 4:1 | 99 | 18 |
| 105 | I.Ba + II-7 | 4 + 1 | 4:1 | 98 | 12 |
| 106 | I.Ca + II-7 | 4 + 1 | 4:1 | 96 | 16 |
| 107 | I.Cb + II-7 | 4 + 1 | 4:1 | 97 | 15 |
| 108 | I.Cc + II-7 | 4 + 1 | 4:1 | 97 | 17 |
| 109 | I.Cd + II-7 | 4 + 1 | 4:1 | 95 | 11 |
| 110 | I.Da + II-7 | 4 + 1 | 4:1 | 96 | 22 |
| 111 | I.Bc + II-7 | 4 + 1 | 4:1 | 95 | 12 |
| 112 | I.Fa + II-7 | 4 + 1 | 4:1 | 80 | 12 |
| 113 | I.Aa + II-8 | 16 + 4 | 4:1 | 83 | 23 |
| 114 | I.Ab + II-8 | 16 + 4 | 4:1 | 97 | 29 |
| 115 | I.Ba + II-8 | 16 + 4 | 4:1 | 96 | 22 |
| 116 | I.Ca + II-8 | 16 + 4 | 4:1 | 93 | 18 |
| 117 | I.Cb + II-8 | 16 + 4 | 4:1 | 66 | 19 |

-continued

| No. | Active substance | Conc. [ppm] | Ratio | Observed effect (%) | Calculated Colby effect (%) |
|---|---|---|---|---|---|
| 118 | I.Cc + II-8 | 16 + 4 | 4:1 | 92 | 31 |
| 119 | I.Cd + II-8 | 16 + 4 | 4:1 | 79 | 22 |
| 120 | I.Da + II-8 | 16 + 4 | 4:1 | 86 | 37 |
| 121 | I.Bc + II-8 | 16 + 4 | 4:1 | 98 | 23 |
| 122 | I.Fa + II-8 | 16 + 4 | 4:1 | 94 | 17 |
| 123 | I.Aa + II-10 | 1 + 0.25 | 4:1 | 50 | 14 |
| 124 | I.Ab + II-10 | 1 + 0.25 | 4:1 | 49 | 13 |
| 125 | I.Ba + II-10 | 1 + 0.25 | 4:1 | 56 | 18 |
| 126 | I.Ca + II-10 | 1 + 0.25 | 4:1 | 43 | 11 |
| 127 | I.Cb + II-10 | 1 + 0.25 | 4:1 | 57 | 12 |
| 128 | I.Cc + II-10 | 1 + 0.25 | 4:1 | 92 | 17 |
| 129 | I.Cd + II-10 | 1 + 0.25 | 4:1 | 60 | 14 |
| 130 | I.Da + II-10 | 1 + 0.25 | 4:1 | 59 | 16 |
| 131 | I.Bc + II-10 | 1 + 0.25 | 4:1 | 69 | 11 |
| 132 | I.Fa + II-10 | 1 + 0.25 | 4:1 | 56 | 14 |

Use Example 9

Activity in the Microtiter Test Against the Pathogen Causing *Septoria* Leaf Spot Disease, *Septoria tritici* (Septtr)

The stock solution is pipetted into a microtiter plate (MTP) and diluted with an aqueous, malt-based fungal nutrient medium to the active substance concentration stated. An aqueous spore suspension of *Septoria tritici* was then added. The plates were placed into a water-vapor-saturated chamber at temperatures of 18° C. The MTPs were measured on day 7 post-inoculation at 405 nm, using an absorption photometer.

The evaluation was analogously to use example 8.

| No. | Active substance | Conc. [ppm] | Ratio | Observed effect (%) | Calculated Colby effect (%) |
|---|---|---|---|---|---|
| 133 | Cycloxydim (I.Ba) | 63 | | 39 | |
| 134 | II-1 | 16 | | 12 | |
| 135 | I.Ba + II-1 | 63 + 16 | 4:1 | 71 | 46 |

It can be seen from the experimental results that, due to the synergism, the mixtures according to the invention are considerably more active than calculated in advance using Colby's formula.

What is claimed is:

1. An active substance combination comprising
   1) at least one herbicide selected from the following groups
      A) glyphosate derivatives I.A, selected from the group consisting of:
         a) glyphosate, of the formula I.Aa,

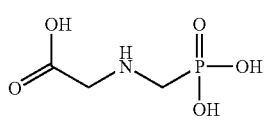

I.Aa b) glufosinate, of the formula I.Ab,

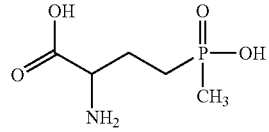

I.Ab and c) glufosinate-ammonium, of the formula I.Ac,

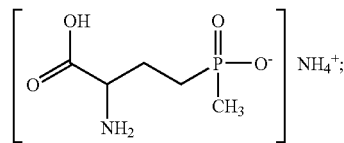

I.Ac

B) cyclohexenone oximes I.B, selected from the group consisting of:
   a) cycloxydim, of the formula I.Ba,

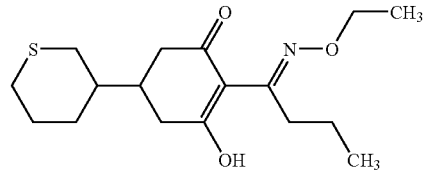

I.Ba b) clethodim, of the formula I.Bb,

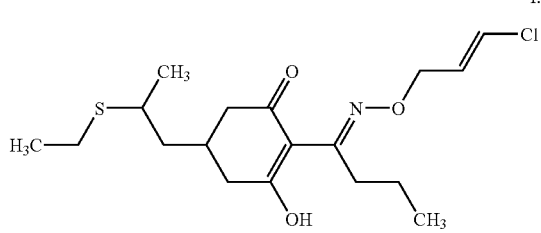

I.Bb c) sethoxydim, of the formula I.Bc,

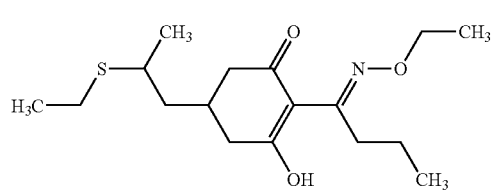

I.Bc d) profoxydim, of the formula I.Bd,

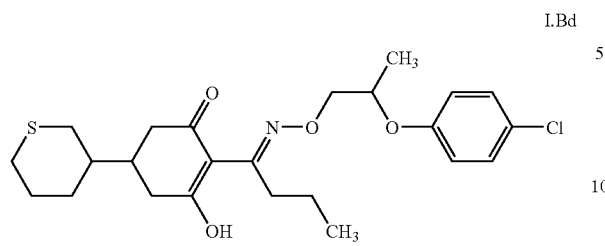

I.Bd and
e) tralkoxydim, of the formula I.Be,

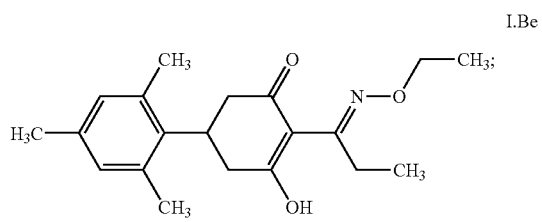 [SMILES: CCO/N=C(\CC)C1=C(O)CC(c2c(C)cc(C)cc2C)CC1=O]

I.Be

C) imidazolinone derivatives 1.C, selected from the group consisting of:
a) imazapyr, of the formula I.Ca,

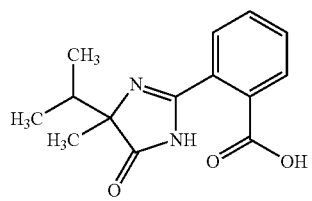

I.Ca b) imazethapyr, of the formula I.Cb,

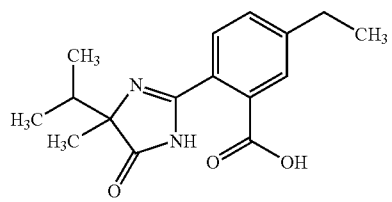

I.Cb c) imazaquin, of the formula I.Cc,

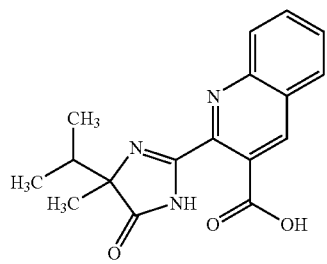

I.Cc d) imazapic, of the formula 1.Cd,

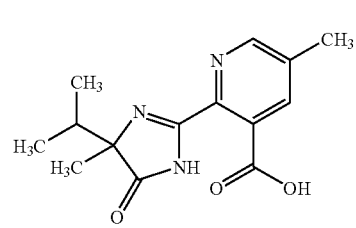

I.Cd and
e) imazamox, of the formula I.Ce,

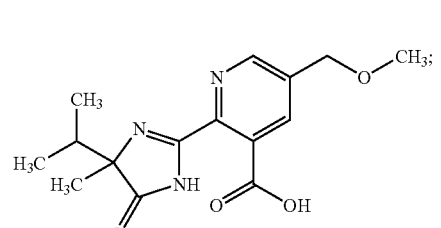

I.Ce

D) dinitroanilin derivatives I.D,
a) pendimethalin, of the formula I.Da,

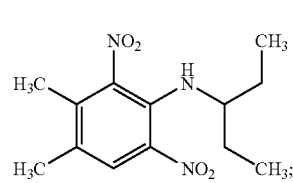

I.Da

E) amide derivatives I.E,
a) dimethenamid-P, of the formula I.Ea,

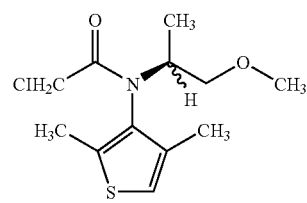

I.Ea

F) quaternary ammonium salts I.F,
a) paraquat, of the formula I.Fa,

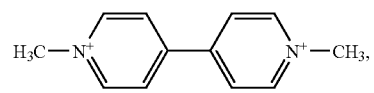

I.Fa and (2) an azolopyrimidinylamine selected from the group consisting of:
6-(3,4-dichlorophenyl)-5-methyl-[1,2,4]triazolo[1,5-a]pyrimidin-7-ylamine, 6-(4-tert-butylphenyl)-5-methyl-[1,2,4]triazolo[1,5-a]pyrimidin-7-ylamine, 5-methyl-6-(3,5,5-trimethylhexyl)[1,2,4]triazolo[1,5-a]pyrimidin-7-ylamine, 5-methyl-6-octyl-[1,2,4]triazolo[1,5-a]

pyrimidin-7-ylamine, 5-ethyl-6-octyl-[1,2,4]triazolo[1,5-a]pyrimidin-2,7-diamine, 6-ethyl-5-octyl[1,2,4]triazolo[1,5-a]pyrimidin-7-ylamine, 5-ethyl-6-octyl-[1,2,4]triazolo[1,5-a]pyrimidin-7-ylamine, 5-ethyl-6-(3,5,5-trimethylhexyl)[1,2,4]triazolo[1,5-a]pyrimidin-7-ylamine, 6-octyl-5-propyl-[1,2,4]triazolo[1,5-a]pyrimidin-7-ylamine, 5-methoxymethyl-6-octyl-[1,2,4]triazolo[1,5-a]pyrimidin-7-ylamine, 6-octyl-5-trifluoromethyl-[1,2,4]-triazolo[1,5-a]pyrimidin-7-ylamine and 5-trifluoromethyl-6-(3,5,5-trimethylhexyl)-[1,2,4]triazolo[1,5-a]pyrimidin-7-ylamine.

2. The active substance combination of claim 1, comprising the herbicide and an azolopyrimidinylamine, of the formula II in a weight ratio of 20:1 to 1:200.

3. A method of treating a transgenic plant, comprising applying an active substance combination of claim 1, to said plant.

4. The method of claim 3, wherein said transgenic plant is a herbicide-tolerant plant.

5. The method of claim 4, wherein said active substance combination comprises as component 1, an imidazolinone derivative I.C, and said plant tolerates imidazolinones.

6. A method of controlling undesirable phytopathogenic fungi, wherein active substance combinations of claim 1, are applied to the undesirable phytopathogenic fungi and/or their habitat and/or seed.

7. The method of claim 3, wherein said plant is a transgenic soybean plant.

8. The method of claim 7, wherein said transgenic soybean plants are resistant to glyphosate, glufosinate or glufosinate-ammonium.

9. A method of controlling undesirable phytopathogenic fungi, wherein active substance combinations according to claim 1, are applied to rust fungi and/or their habitat and/or seed.

10. The method of claim 9, wherein said rust is one or more rust diseases on soybean plants.

11. The method of claim 10, wherein said soybean plant is a transgenic soybean plant.

12. A process for the preparation of pesticidal compositions, wherein active substance combinations of claim 1, are mixed with extenders and/or surfactants.

13. A seed-dressing product comprising an active substance combination of claim 1.

14. The method of claim 9, wherein said seed is a transgenic seed.

15. The method of claim 3, wherein said transgenic plant is a herbicide-sensitive plant.

16. The active substance combination of claim 1, comprising, as component 1, a glyphosate derivative I.A.

17. The active substance combination of claim 1, comprising glyphosate I.Aa.

18. The active substance combination of claim 1, comprising glufosinate I.Ab.

19. The active substance combination of claim 1, comprising glufosinate-ammonium I.Ac.

20. The active substance combination of claim 1, comprising, as component 1, a cyclohexenone oxime I.B.

21. The active substance combination of claim 1, comprising, as cyclohexenone oxime, an active substance selected from the group consisting of cycloxydim I.Ba and clethodim I.Bb.

22. The active substance combination of claim 1, comprising, as component 1, an imidazolinone derivative I.C.

23. The active substance combination of claim 1, comprising, as imidazolinone derivative, an active substance selected from the group consisting of imazapyr I.Ca, imazethapyr I.Cb, imazaquin I.Cc and imazapic I.Ce.

24. The active substance combination of claim 1, comprising, as component 1, pendimethalin I.Da.

25. The active substance combination of claim 1, comprising, as component 1, dimethenamid-P I.Ea.

26. The active substance combination of claim 1, comprising, as component 1, paraquat I.Fa.

27. The active substance combination of claim 1, comprising paraquat dichloride.

\* \* \* \* \*

UNITED STATES PATENT AND TRADEMARK OFFICE
CERTIFICATE OF CORRECTION

PATENT NO. : 8,461,077 B2
APPLICATION NO. : 12/532078
DATED : June 11, 2013
INVENTOR(S) : Christine Habicher et al.

It is certified that error appears in the above-identified patent and that said Letters Patent is hereby corrected as shown below:

In the Claims
In claim 1,
  col. 35, line 28, delete "1.C" and insert therefore --I.C--; and
  col. 36, line 1, delete "1.Cd" and insert therefore --I.Cd--.

Signed and Sealed this
Fourteenth Day of January, 2014

Michelle K. Lee
*Deputy Director of the United States Patent and Trademark Office*